United States Patent
Wood et al.

(10) Patent No.: US 6,925,200 B2
(45) Date of Patent: Aug. 2, 2005

(54) GRAPHICAL USER INTERFACE FOR DISPLAY OF ANATOMICAL INFORMATION

(75) Inventors: Susan A. Wood, Mountain View, CA (US); Heidi Zhang, San Jose, CA (US); Anat Caspi, San Francisco, CA (US); Takeshi Doi, Palo Alto, CA (US); Harlan M. Romsdahl, Half Moon Bay, CA (US)

(73) Assignee: R2 Technology, Inc., Sunnyvale, CA (US)

( * ) Notice: Subject to any disclaimer, the term of this patent is extended or adjusted under 35 U.S.C. 154(b) by 747 days.

(21) Appl. No.: 09/990,511

(22) Filed: Nov. 21, 2001

(65) Prior Publication Data

US 2002/0070970 A1 Jun. 13, 2002

Related U.S. Application Data

(60) Provisional application No. 60/314,582, filed on Aug. 24, 2001, and provisional application No. 60/252,743, filed on Nov. 22, 2000.

(51) Int. Cl.$^7$ ................................................ G06K 9/00
(52) U.S. Cl. ..................................... 382/132; 715/700
(58) Field of Search ............................... 382/128, 129, 382/130, 131, 132, 133, 134; 600/407, 410, 443, 447; 378/4, 62; 725/762

(56) References Cited

U.S. PATENT DOCUMENTS

| | | | |
|---|---|---|---|
| 4,851,984 A | | 7/1989 | Doi et al. |
| 4,908,876 A | | 3/1990 | DeForest et al. |
| 5,168,531 A | | 12/1992 | Sigel |
| 5,222,499 A | | 6/1993 | Allen et al. |
| 5,435,310 A | * | 7/1995 | Sheehan et al. ............ 600/416 |
| 5,891,030 A | | 4/1999 | Johnson et al. |
| 5,986,662 A | | 11/1999 | Argiro et al. |
| 5,987,345 A | | 11/1999 | Engelmann et al. |
| 6,169,817 B1 | * | 1/2001 | Parker et al. ............... 382/131 |
| 6,272,366 B1 | * | 8/2001 | Vining ........................ 600/407 |
| 6,366,796 B1 | * | 4/2002 | Yanof et al. ................ 600/407 |
| 6,366,800 B1 | | 4/2002 | Vining et al. |
| 6,544,178 B1 | * | 4/2003 | Grenon et al. .............. 600/443 |

* cited by examiner

*Primary Examiner*—Kanjibhai Patel
*Assistant Examiner*—Abolfazl Tabatabai
(74) *Attorney, Agent, or Firm*—Morgan, Lewis & Bockius LLP

(57) ABSTRACT

A computer-aided diagnostic method and system provide image annotation information that can include an assessment of the probability, likelihood or predictive value of detected or identified suspected abnormalities as an additional aid to the radiologist. More specifically, probability values, in numerical form and/or analog form, are added to the locational markers of the detected and suspected abnormalities. The task of a physician using such a system as disclosed is believed to be made easier by displaying markers representing different regions of interest.

73 Claims, 35 Drawing Sheets

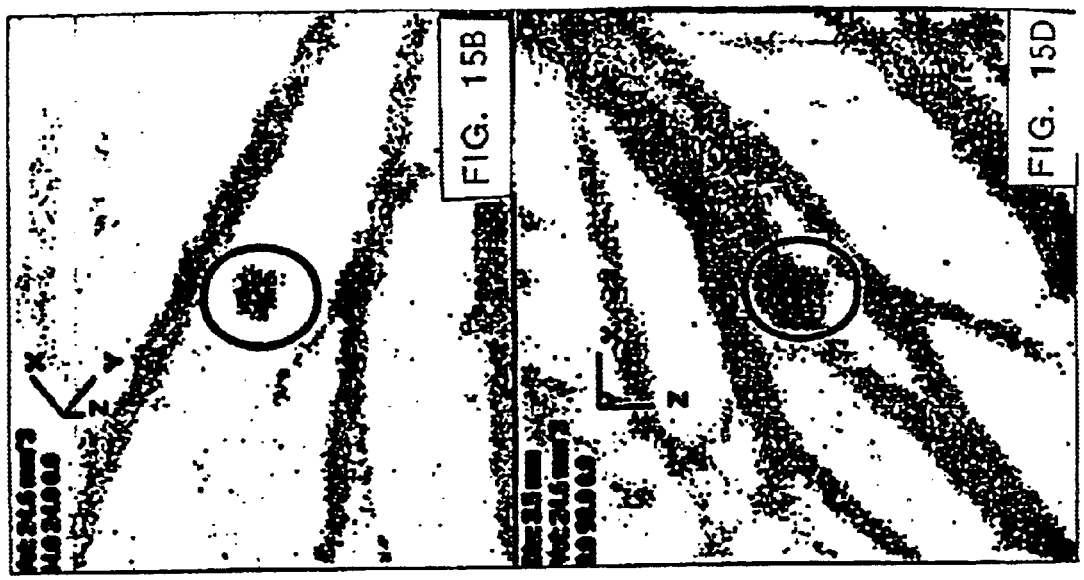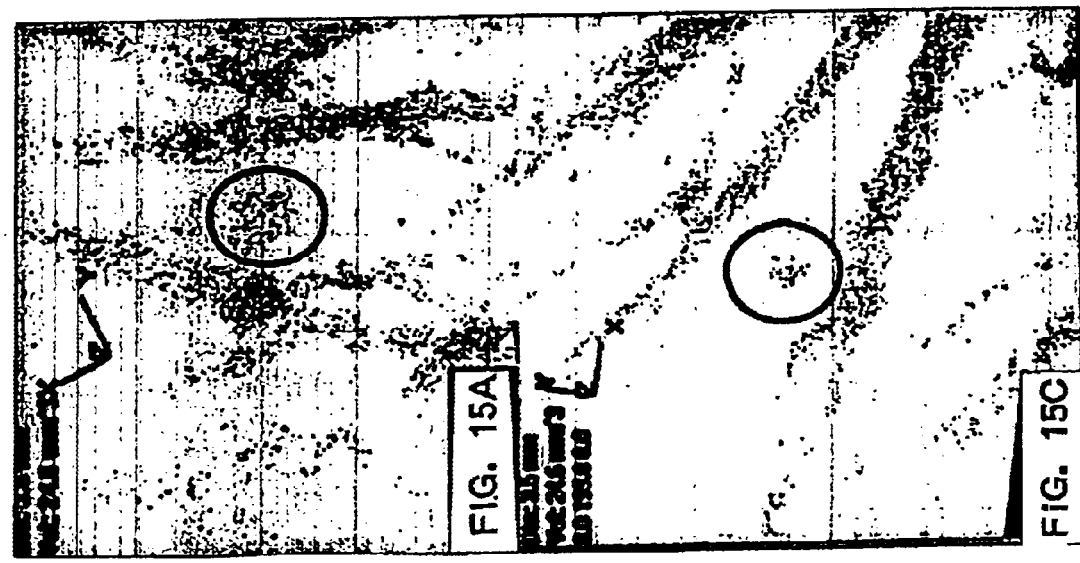

GRAPHICAL USER INTERFACE FOR DISPLAY OF ANATOMICAL INFORMATION

CROSS REFERENCE TO RELATED APPLICATIONS

The present application claims priority to the U.S. Provisional Application Ser. No. 60/314,582 filed Aug. 24, 2001, and claims priority to U.S. Provisional Application Ser. No. 60/252,743, filed Nov. 22, 2000.

FIELD OF THE INVENTION

This relates to a system for rendering anatomical information. It is particularly useful in the display of computer tomographic information and will be described in that context.

BACKGROUND OF THE INVENTION

In conventional x-ray systems, a beam of x-rays is directed through an object such as the human body onto a flat x-ray photographic film. The beam of x-rays is selectively absorbed by structures within the object, such as bones within the human body. Since the exposure of the x-ray film varies directly with the transmission of x-rays through the body (and varies inversely with the absorption of x-rays), the image that is produced provides an accurate indication of any structures within the object that absorbed the x-rays. As a result, x-rays have been widely used for non-invasive examination of the interior of objects and have been especially useful in the practice of medicine.

Unfortunately, conventional x-ray systems have their limitations. The image that is formed from the x-ray is basically the shadow of the structures within the object that absorb the x-rays. As a result, the image formed on the x-ray is only two-dimensional, and if multiple x-ray absorbing structures lie in the same shadow, information about some of these structures is likely to be obscured. Moreover, in the case of medical applications, it is often quite difficult to use conventional x-ray systems to examine portions of the body such as the lungs that consist mostly of air when inflated and do not absorb x-rays significantly.

Many of the limitations of conventional x-ray systems are avoided by x-ray computer tomography, which is often referred to as CT. In particular, CT provides three-dimensional views and the imaging of structures and features that are unlikely to be seen very well in a conventional x-ray.

A typical CT apparatus 100 for medical applications is shown in FIG. 1. This apparatus includes a computer 110, a large toroidal structure 120 and a platform 130 that is movable along a longitudinal axis 140 through the center of the toroidal structure. Mounted within the toroidal structure are an x-ray source (not shown) and an array of x-ray detectors (not shown). The x-ray source is aimed substantially at the longitudinal axis and is movable around the interior of the toroidal structure in a plane that is substantially perpendicular to the longitudinal axis. The x-ray detectors are mounted all around the toroidal structure in substantially the same plane as the x-ray source and are aimed at the longitudinal axis. To obtain a CT x-ray image, a patient is placed on the platform and the platform is inserted into the center of the toroidal structure. The x-ray source then rotates around the patient continuously emitting x-rays and the detectors sense the x-ray radiation that passes through the patient. Since the detectors are in the same plane as the x-ray source, the signals they receive relate essentially to a slice through the patient's body where the plane of the x-ray source and detectors intersect the body. The signals from the x-ray detectors are then processed by the computer to generate an image of this slice known in the art as an axial section. Examples of CT axial sections of the thorax are shown in FIGS. 11A–11G.

How this image is generated will be more readily apparent from the simplified explanation of FIG. 2. For purposes of illustration we will consider x-rays emitted from only three points 252, 254, 256 within a toroidal structure 220 in a plane coincident with the plane of the drawing. A platform 240 is movable along an axis 230 perpendicular to the plane of the drawing. Each of points 252, 254, 256 is located on the toroidal structure approximately 120° of arc from the other two points and the beam of x-rays diverges toward the axis 230. An array of x-ray detectors 260 extends around the toroidal structure in the same plane as the x-ray source. If we assume that there is an object on the platform that has an x-ray absorbing feature 270, we can see from FIG. 2 how this feature can be detected and located. The detector array will detect the shadow cast by feature 270 in portions 252A, 254A, and 256A of the x-rays emitted from sources 252, 254 and 256, respectively. However, it will also detect that there was no absorption in regions 252 B&C, 254 B&C and 256 B&C. The failure to detect absorption in regions 252 B&C indicates that the dimension of the feature 270 along the line extending from source 256 to the detectors in the region 256A is simply the projection of region 252A onto that line. Similarly, the dimensions of the feature along the lines from source 252 to region 252A and from source 254 to region 254A can be determined. And from these calculations the shape and location of feature 270 can be determined.

In practice, x-rays are emitted continuously for the full 360° around the patient and numerous features are observed but the overall approach is generally the same.

While the patient remains motionless, the platform is moved along the longitudinal axis through the toroidal structure. In the course of this movement, x-ray exposures are continuously made of the portion of the patient on which CT is to be performed. Since the table is moving during this process, the different x-ray exposures are exposures of different slices of the portion of the patient being examined and the images generated by the computer are a series of axial sections depicting in three dimensions the portion of the patient's body that is being examined. The spacing between adjacent CT sections depends on the minimum size of the features to be detected. For detection at the highest resolution, center-to-center spacing between adjacent sections should be on the order of less than 2 mm.

Because of the superior imaging capabilities of CT, the use of CT in medical imaging has grown rapidly in the last several years due to the emergence of multi-slice CT. However, the cost of conventional CT equipment remains quite high (an average selling price in the United States of $800,000 per unit) and the cost per patient far exceeds the cost of a conventional x-ray.

One application of medical CT is detection and confirmation of cancer. Unfortunately, in all too many cases, this application is merely to confirm the worst. By the time a patient has symptoms enough that warrant the use of CT, the cancer detected by CT has progressed to the point that the patient is almost certain to die of the cancer.

The diagnostically superior information now available in CT axial sections, especially that provided by multidetector CT (multiple slices acquired per single rotation of the gantry) where acquisition speed and volumetric resolution provide exquisite diagnostic value, however, enables the detection of potential cancers at the earliest and most treatable stage. For example, the minimum detectable size of a potentially cancerous nodule in an axial section of the lung is about 2 mm (1/10 of inch), a size that is potentially treatable and curable if detected. To intercept a developing cancer in the time between the point at which it first becomes detectable and treatable and the time when it has grown to the point where it is no longer treatable or treatment is pointless; it may become necessary to screen the population at risk on a regular basis. Presently, the standard of care is to find all cancer and potential cancers at their earliest indication. Finding a cost effective way to screen the population for lung cancer remains challenging.

While costs/benefits are such that it is prohibitive to screen the entire population for cancer, there are sub-populations that are at greater risk for cancer than others. One such population is that of present or former smokers. Other such populations are those with occupational exposures to known or suspected carcinogens. For these populations the cost/benefit ratio is such that the use of CT for screening purposes may well be warranted.

Tools that enhance the diagnostic value of the CT scans as well as enable the diagnostic determination by a radiologist in an economically reasonable time are required to assist the physician in the effort to detect cancer at its earliest and most curable stage. These tools are required whether the original examination was performed as a screening or non-screening study.

SUMMARY OF THE INVENTION

The present invention is a system for displaying anatomical information automatically detected by computer algorithms (computer-aided detection, or CAD), such anatomical information generated by tomographic scanning of the body (i.e., CT, MRI, ultrasound, PET). The CAD system provides for the display of detected objects in any selected viewport.

In a preferred embodiment, the system is responsive to system user inputs in various display portions of a user interface. For example, one portion of an interface renders, or displays, a sequence of tomographic sections, the particular section or sections being displayed at any time being selectable by a scroll bar or scroll buttons. An additional portion of the interface display renders a volumetric view of a body including an indication on the view of a position on the body corresponding to the tomographic section then being rendered, or displayed, on the first portion of the display. An additional portion of the display renders a volumetric view of a selected feature shown in the section then being rendered, or displayed, on the first portion of the display. The portions are designed to optimize the speed and accuracy with which the end user can diagnose the case. Optimization results from the mapping of the volumetric information, inherent to understanding the structure and function of a region under review, to the normal two-dimensional, axial reading paradigm currently used by the radiologists reviewing these types of case sets. Also inherent to this optimization is that an automatically-detected portion of the system is mapped in all portion views.

The invention also includes the method of providing such a graphical user interface.

BRIEF DESCRIPTION OF THE DRAWINGS

These and other objects, features and advantages of the invention will be more readily apparent from the following Detailed Description of the Invention in which:

FIGS. 15A–15D are an illustrative series of views seen in a third portion of the display of FIG. 5;

DETAILED DESCRIPTION OF THE INVENTION

Figure 1:
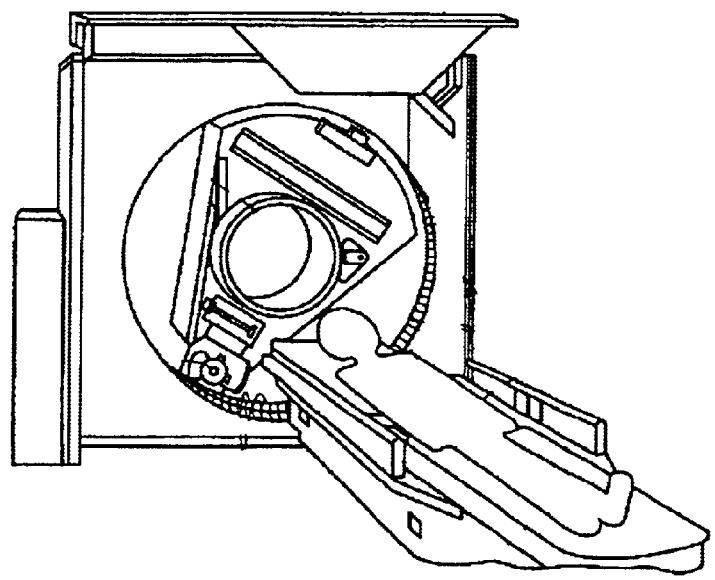
FIG. 1 is an illustration of a conventional CT system.
Figure 2:
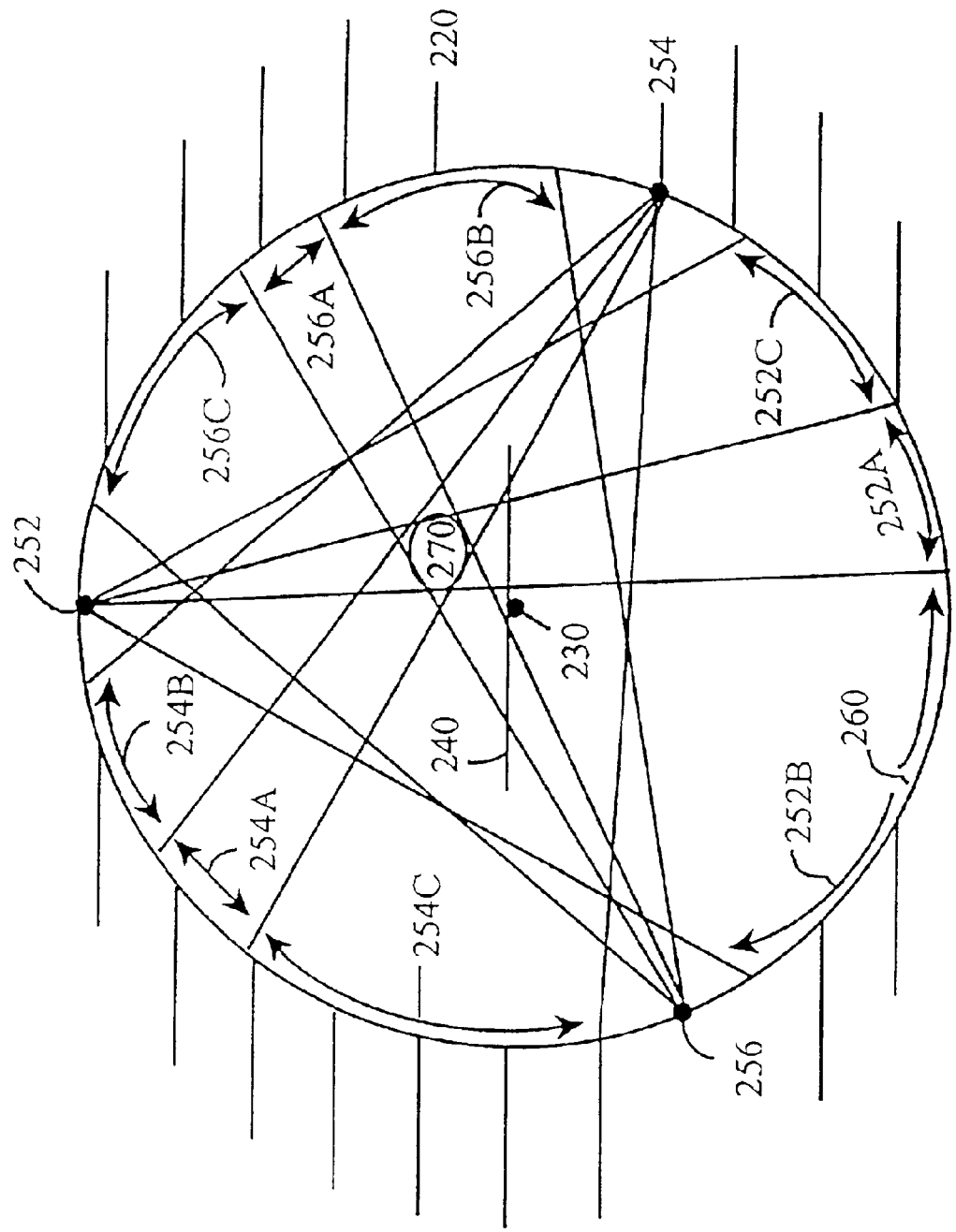
FIG. 2 is a sketch useful in understanding the operation of a CT system.
Figure 3:
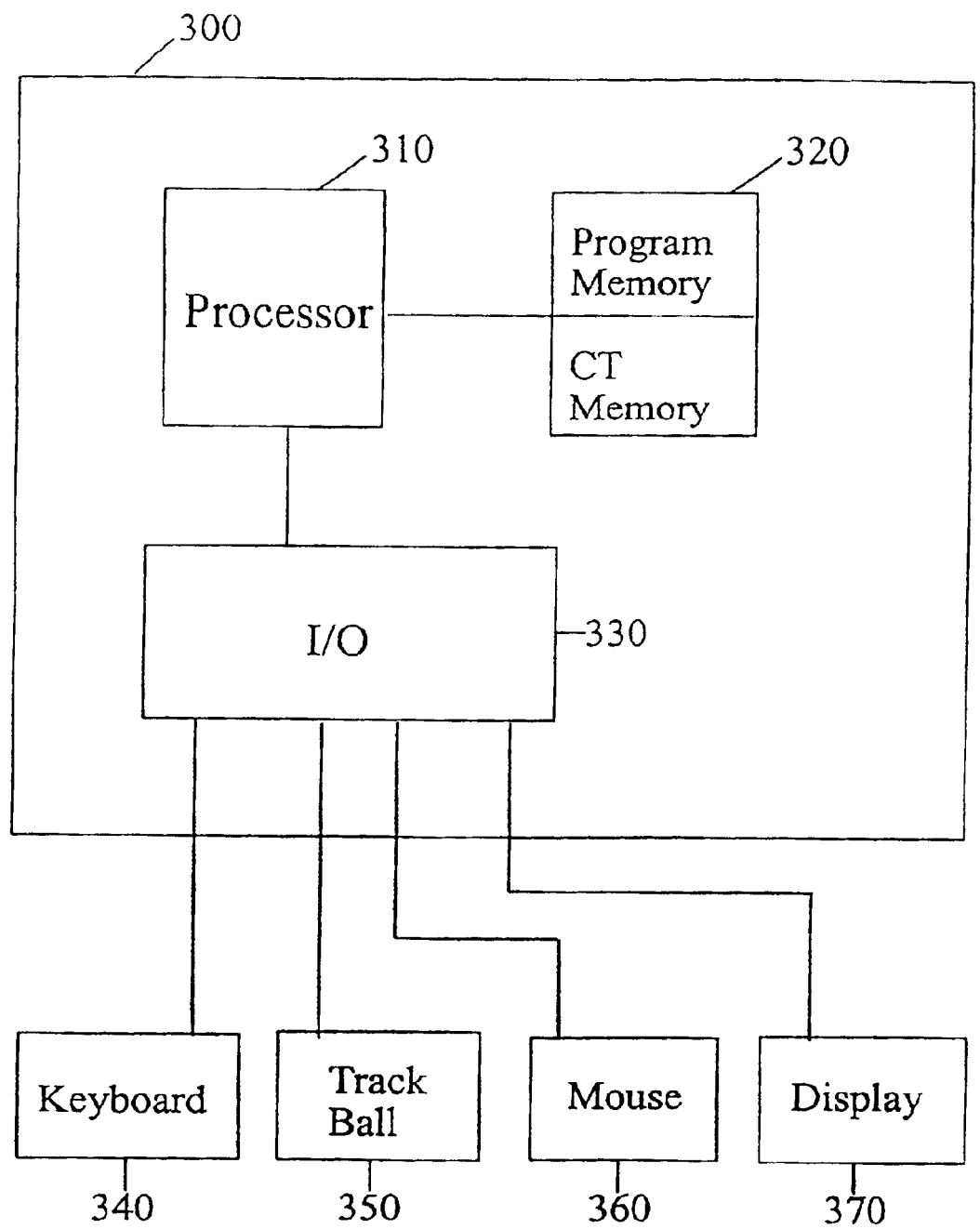
FIG. 3 is a block diagram of a conventional computer system on which the invention may be practiced.

FIG. 3 is a block diagram of an illustrative computer system 300 useful in the practice of the invention. As shown, system 300 comprises a processor 310, a memory 320 and input/output interface 330. The input/output interface connects the processor to an input device (such as keyboard 340, a trackball 350, a mouse 360 and/or any other device capable of communicating and/or processing commands and inputs to the processor) and a display monitor 370. Illustratively, the processor is a 500 MHZ Intel Pentium III (Reg. TRANSCEIVER MODULE) dual microprocessor.

Memory 320 typically is a mixture of semiconductor random access memory (RAM), one or more hard disk drives and/or CD-ROM drives, perhaps a floppy drive, and one or more tape drives. Stored within memory 320 are an operating system, application programs and the data representative of one or more series of CT (or other three-dimensional datasets like MRI, ultrasound, PET) sections of one or more patients. Each series of CT sections is referred to as a case. A complete case might have 200 or more CT sections to provide a high resolution three-dimensional representation of a portion of the body as large as the thorax. Advantageously, several such cases are available in memory 320 and can be selected by the physician for examination.

Figure 4:
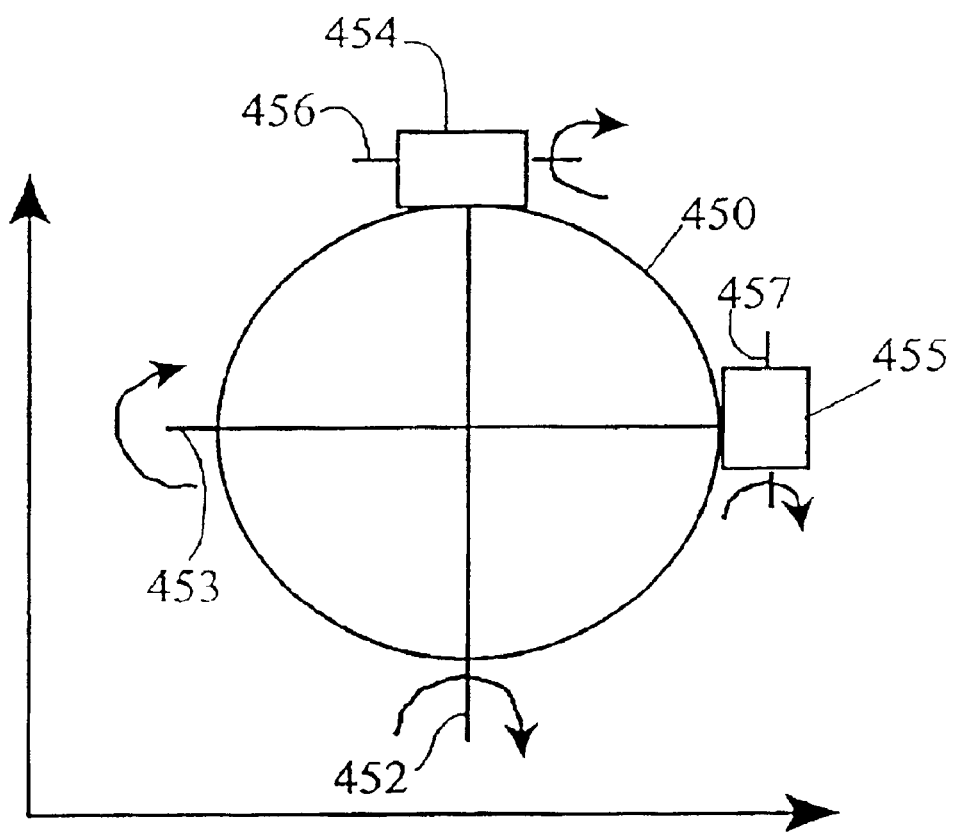
FIG. 4 is a sketch illustrating the operation of a mouse or trackball.

FIG. 4 is a diagram useful in understanding the operation of trackball 350. The ball of the trackball is shown in cross-section in FIG. 4 as circle 450. The trackball is rotatable in substantially any direction including about axes 452 and 453 that are perpendicular to each other and in the plane of the drawing. The trackball engages at least two pick-up wheels 454 and 455 that rotate about axes 456 and 457, respectively, that are parallel to axes 452, 453, respectively. The pick-up wheels separate the motion of the trackball into motion in two perpendicular dimensions and convert this motion into electrical signals proportional to such motion. Thus, if the trackball were to be rotated about axis 452, the motion of the trackball would cause motion of the pick-up wheel 454 and that motion would be converted to an electric signal. Pick-up wheel 455 operates similarly with respect to motion of the trackball about axis 453. The operation of mouse 360 is similar.

Figure 5:
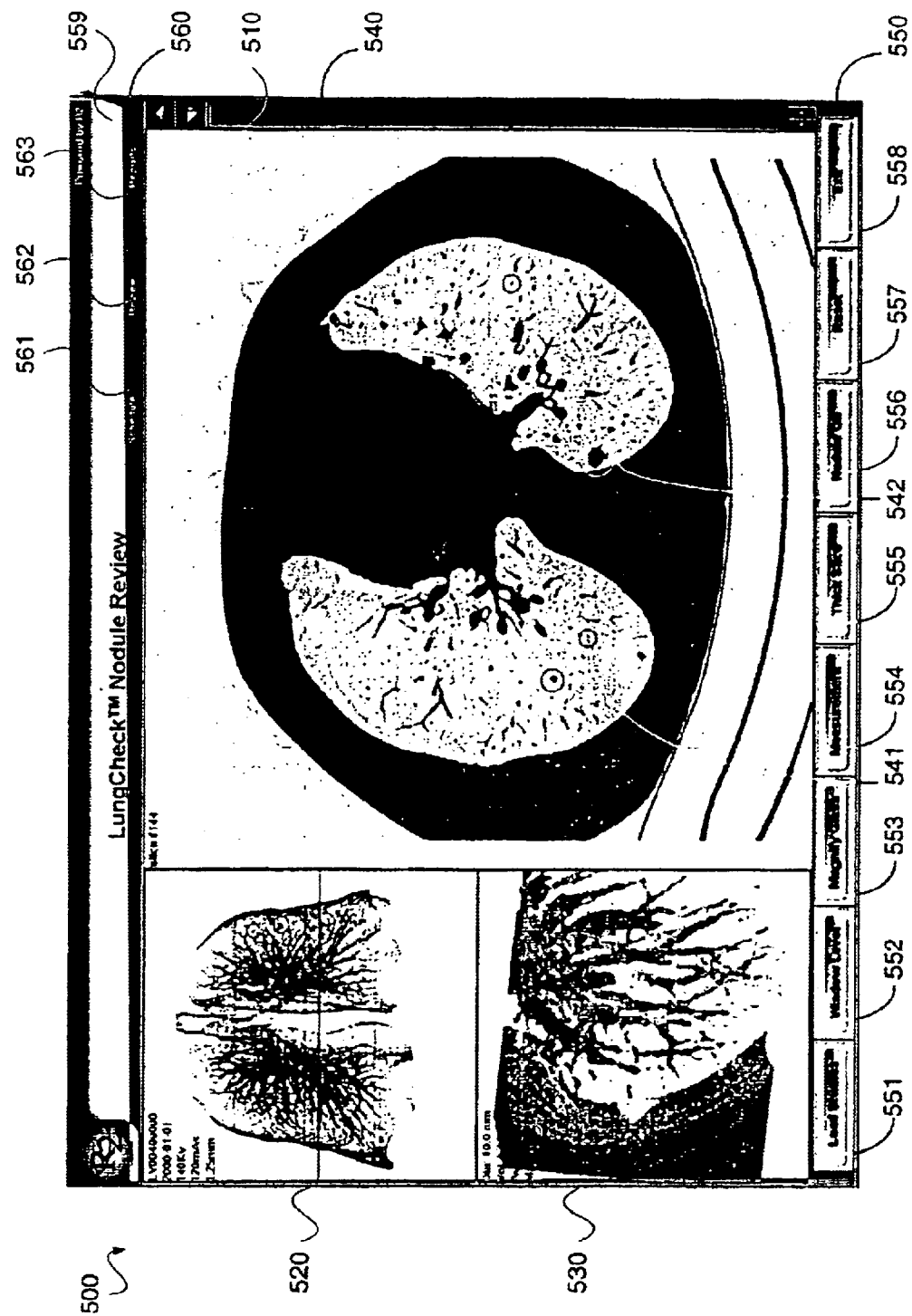
FIG. 5 is an illustration of a computer display of a preferred embodiment of the invention.

FIG. 5 depicts an illustrative embodiment of a display 500 of the present invention as generated on display screen 370. Display 500 includes: a first display 510 of CT sections, a second display 520 that is a volumetric view of the volume encompassed by the CT sections, and a third display 530 that is a magnified and rotatable portion of part of the volume rendered in the second display. The display system generates the volumetric view from the series of two-dimensional CT sections of an organ (or portion of the human anatomy) displayable in the first display. In the embodiment illustrated in FIG. 5, the volumetric displays 520, 530 display the structure of the vessels shown in the axial CT sections. Display 520 is a view of the entire region encompassed by the CT sections while display 530 is a magnified and rotatable portion of one small region. Display 520 makes it possible to visualize the overall structure of the vessels. Display 530 helps the physician establish whether a particular fleck is connected to a vessel or is isolated therefrom as in the case of the dot in the center of display 530.

The preferred display system provides for the display of any one or more of the three display portions and enables the user to toggle on-off any of the display portions. In the event any display portion is not shown, the remaining display portions may be re-sized. Accordingly, while FIG. 5 depicts the rendering of images in three display portions, it will be understood that only one or two display portions may be displayed at the option of the user.

Any type of digital or digitized image (CT, MRI, US, SPECT, PET) is amenable to the processing and rendering of images and views of any organ system. The tomographic sections to be processed, rendered, displayed or otherwise used includes tomographic sections acquired through any plane, including, without limitation, saggital, coronal and axial (or horizontal, transverse) planes and including planes at various angles to the saggital, coronal or axial planes. While the disclosure may refer to a particular plane or section, such as an axial section or plane, it is to be understood that any reference to a particular plane is not necessarily intended to be limited to that particular plane, as the invention can apply to any plane or planar orientation. Additionally, the interface application disclosed herein enables interactive two-dimensional and three-dimensional rendering of an organ or organ system (including, without limitation, lung, heart, brain, spinal, colon, liver and kidney systems) which enables user interaction with the imagery. For illustrative purposes, a lung system is described.

In a preferred embodiment, the first display and second display are related to one another, for example, based on a common region of interest. As will be further discussed herein, one possible implementation of the inter-relationship of the first and second display is for the second display to use a horizontal line as shown in FIG. 5 to highlight on the volumetric view the relative location of a computer or physician detected region of interest shown in the first display. As various images are rendered in the first display, the location of the horizontal line in the image in the second display will correspondingly change in response thereto. The first display may also be responsive to inputs made in the second display. For example, in one approach the image rendered in the first display can be a CT section selected by moving a reference plane in the second display. The third display can similarly be linked to the first and/or second displays so that each of the first, second and/or third displays is related and is responsive to inputs received by any other display. For example, computer or physician-detected regions of interest (possibly indicating a suspicious nodule) selected in one display can be appropriately indicated in any other display viewport. And, as shown in FIG. 5, the third display displays a magnified and rotatable portion of part of the volumetric view depicted in the second display and associated with the CT section rendered in the first display. It is possible to provide such inter-responsiveness among a first display, second display, third display and so on because the volumes and images rendered are constructed and derived from the same sequence of axial sections.

In a preferred embodiment, the display also includes a lesion navigator 540 (shown on the righthand side of FIG. 5) for selecting different computer or physician detected regions of interest in the acquired dataset or selecting a particular nodule for display in another display portion. Navigating, or scrolling, through the selector automatically updates all axial and volumetric display viewports (or display portions) in which a computer or physician detected suspicious region of interest is located. For example, and explained further below in regards to FIG. 16, the navigator can include scroll bars and/or buttons to facilitate selection of a desired CT section. A navigator can be configured to interact with any of the first, second or third display portions or multiple navigators can be employed, each associated with a display. A navigator can include one or more identifiers associated with one or more markers. Clicking or selecting an identifier causes display of the image or CT section associated with the identifier, facilitating the selection and rendering of a desired image or CT section.

The CT sections display in a gray scale the regions of the body that have absorbed x-rays. In FIG. 5, the CT section is a section of the thorax. The dark enclosed regions are the air-filled lungs. The whitest sections are bone with the spine being displayed in the bottom center of the section and the bones of the rib cage surrounding the lungs. The remaining gray regions are muscle, fat and skin with the most prominent feature being the globular mass of the heart. In the case of the gray regions, x-ray absorption is primarily attributable to the presence of fluids in these regions.

Within the lungs are numerous gray flecks. For the most part, these flecks are sections of blood vessels within the lung that have absorbed sufficient x-rays to be visible in the gray scale image. These vessels can be identified by finding contiguously aligned flecks in adjacent axial sections and following such structures through the axial CT sections long enough to establish that they are indeed sections of blood vessels. Some flecks, however, may be cancerous nodules. These are generally recognizable by their globular shape and their isolation from the vesicular structures in the lung. Two such cancerous nodules are identified by circles, such as circles 541 and 542, in display 510.

In the prior art, a physician scans through a series of axial CT sections relying on visual memory to establish the connectivity of the vesicular structures and looking for the isolated flecks that may be sections of cancerous nodules. Typically, this type of scan is done in a minute or less. In view of the complexity of the structures present in the axial sections, it can be appreciated that this is a difficult task and one in which cancerous nodules can frequently be overlooked.

The display system can include markers or other graphic representations to assist the user in examination of the displays; and the image rendered in a first, second or third display can be controlled by the selection of a marker in a first, second or third display. For example, the second display may include one or more such markers highlighting and associated with various regions of the volumetric view; and a CT section associated with a marker selected in the second display may be rendered in the first display. Similarly, a rendering in the third display is preferably responsive to the selection of a marker from the first or second display.

In a preferred embodiment of the invention, display 500 generates a variety of markers including highlighted markers 541, 542 and line segments on scroll bar 540. Such markers identify potential regions of interest as determined by image processing steps performed, for example, by processor unit 310 and are intended to direct the attention of qualified personnel to suspicious areas. In one preferred embodiment, the digital image in the first display, second display and/or third display will have marker(s) or other identifiers such as an asterisk (*), triangle or configurable circles (shown as 541, 542) superimposed on those locations corresponding to suspicious regions, detected automatically by computer or by the physician, and other markers or identifiers superimposed on other regions of interest wherein such other markers or identifiers are preferably visually different (e.g., different shape, size or color).

In the embodiment of the invention shown in FIG. 5, a first marker (e.g. 541 or 542), in this case circular, is shown at the centroid of several regions of interest on a digitized image in the first display. Concurrently, the second display preferably displays a second display marker, such as a horizontal line at a location of the body corresponding to the location associated with the first marker. A third display marker may appear in the third display. However, since the image in the third display is an enlarged view associated with a region of interest, the third display marker preferably takes the form of a highlighted nodule or region of interest displayed in a different color.

As an enhancement, further information may be provided by showing the evaluator exactly which pixels of the image are considered suspicious. For example, pixels of an image may be highlighted with a particular color, such as green or red, or shown white. In an embodiment of the invention, the display device may include a touch screen. In such an embodiment, the evaluator can select to view an area surrounding some highlighted pixels by simply touching the marker on the screen. The system then provides a close up view of the region with the highlighted pixels. Alternatively, the display device may be a cathode ray tube (CRT) connected to an input device such as a keyboard or mouse, and the input device may be used to command the system to provide a close up view and to highlight the suspicious pixels.

Experience has shown that there are situations where the further information provided by highlighted pixels is useful in reducing false positive indications sometimes called "false markers." Computer-aided detection codes use objective data which sometimes leads to these false markers and a possible waste of time for the evaluator. Using the present invention, however, the evaluator's time is much better used. By showing the evaluator exactly which pixels the computer algorithm considered suspicious, and immediately available to the user in 2-D and/or 3-D representations, she can more easily evaluate and dismiss false markers. Furthermore, the present invention allows the evaluator to more readily evaluate true markers corresponding to potentially malignant nodules.

Display 500 further includes an array 500 of software-controlled function buttons that is configurable by the user and typically includes most of the following: a load studies button 551, a window level button 552, a magnify glass button 553, a measurement button 554, a thick slice button 555, a nodule on button 556, a reset button 557 and an exit button 558. Additional buttons can be located on button tab 560 such as schedule button 561, review button 562 and reports button 563. Display 500 can be configured to have button functionality located in various locations, either as part of a tab display, such as button tab 560, or as part of array 550 of function buttons.

Figure 6:
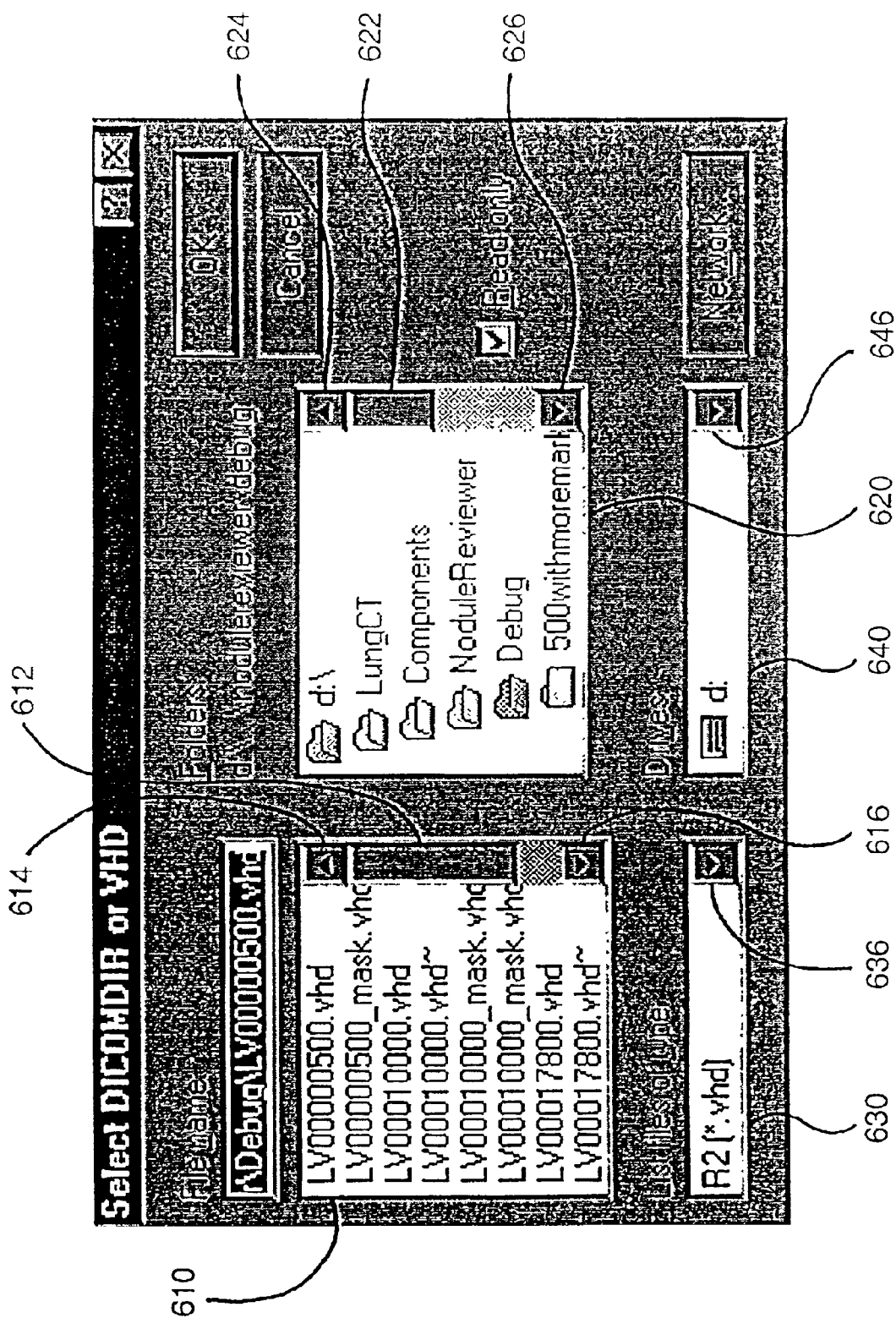
FIGS. 6, 7 and 8 are illustrations of menus that are displayed upon clicking first, second and third buttons on the display of FIG. 5.

The load studies button allows a user to select and load a particular case into the system for viewing. The particular case information may include, without limitation, the patient's name, patient history, detailed patient information or other information related to a test procedure or diagnosis. Upon clicking on this button, a menu is displayed such as that depicted in FIG. 6. The menu has a file name display 610, a folder display 620, a file type display 630, and a drives display 640. The file name display may be scrolled by a scroll bar 612 and up and down buttons 614 and 616. Similarly, the folder display may be scrolled by scroll bar 622 and up and down buttons 624 and 626. The file type display and the drives display may be scrolled by down buttons 636 and 646, respectively.

The drives display 640 allows the user to select a particular hard drive or floppy drive on which is located the data of interest. The folder display 620 displays the folders that are stored on the selected drive and allows the user to select the particular folder in which is located the data of interest. The file name display 610 displays the files (or cases) that are stored in a particular folder and allows the user to select one of these cases for display on display 370. File type display 630 allows the user to filter the files available in a folder.

The window level button 552 allows the user to change the brightness level and contrast level of the display. Clicking on this button activates the left button of the mouse. While the left button is depressed, the mouse or trackball can be moved in one direction so as to change the brightness level and in an orthogonal direction to change the contrast level.

Figure 9A:
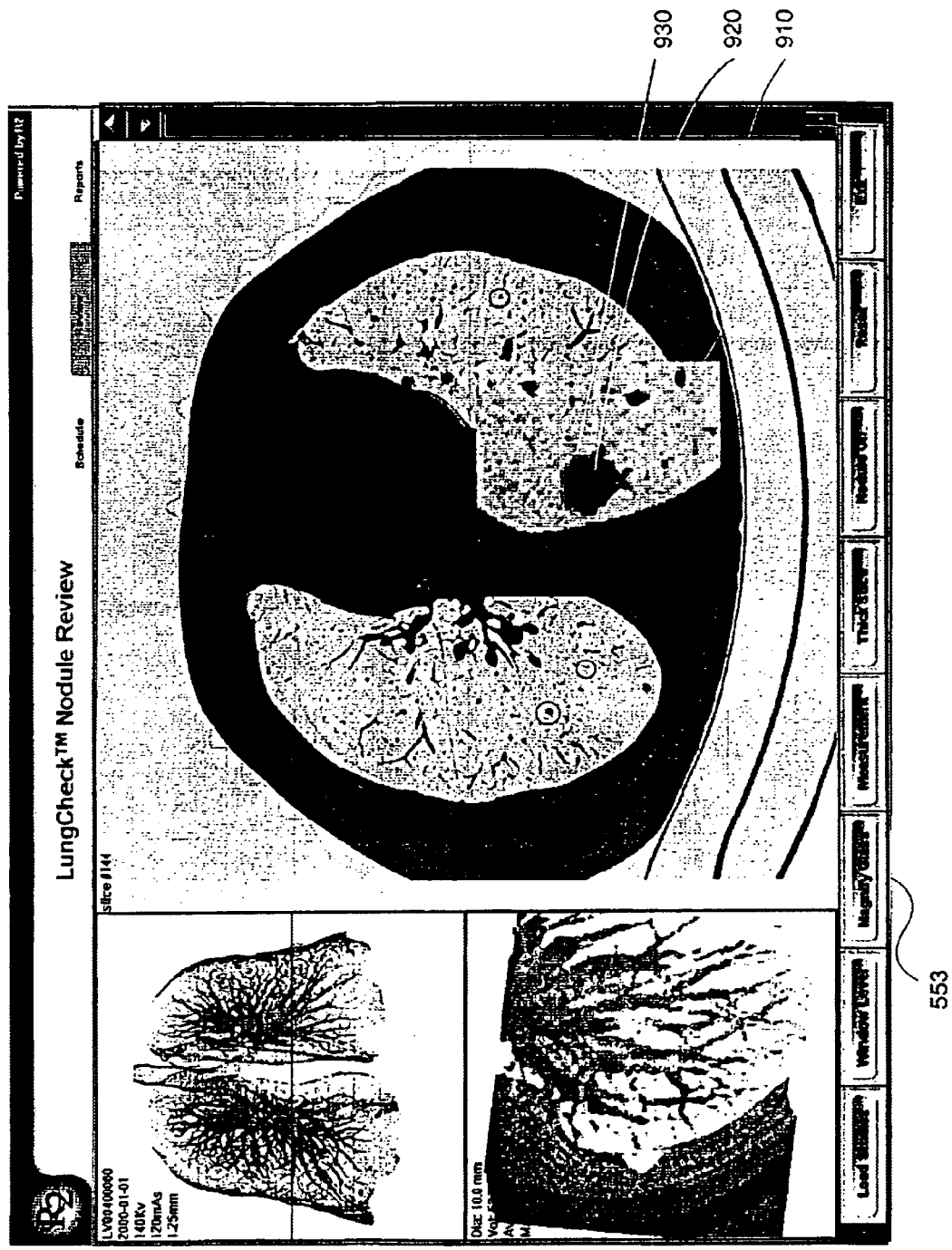
FIG. 9A is an illustration of a magnification feature that is displayed upon clicking a fourth button on the display of FIG. 5.

Clicking on the magnify glass button 553 activates the left button of the mouse. While the left button is depressed, the computer magnifies the display where a mouse-controlled cursor is located as shown in FIG. 9A. By moving the mouse and thereby moving the cursor, the user can change the portion of the display that is magnified. Advantageously, the amount of magnification can be selected by the user and is in the range of approximately 2× to 5×. The region that is magnified is displayed in box 910. In one embodiment, the magnification box is set at a pre-determined size with the box having a center corresponding to the location of the cursor. In an alternative preferred embodiment, the box size is configurable and based on a region of magnification defined by a rectangle formed by locating the cursor at one corner and clicking-and-dragging the cursor to an opposite corner to define the size of the image in the rectangle to be magnified. If the image in the box 910 contains a nodule or object, such as nodule 920, the system can place an outline 930 around the nodule. The outline is formed on the basis of differing contrast levels between the bright nodule and the dark background. For example, if intensity at some reference point is $\emptyset_0$, and at an adjacent point is $\emptyset_1$, the contrast can be defined as $(\emptyset_1-\emptyset_0)/\emptyset_0$. Contrast can also be expressed in terms of energy fluence or exposure. The outline allows for evaluation of the shape of the nodule and allows for detailed measurement of the nodule.

Figure 9B:
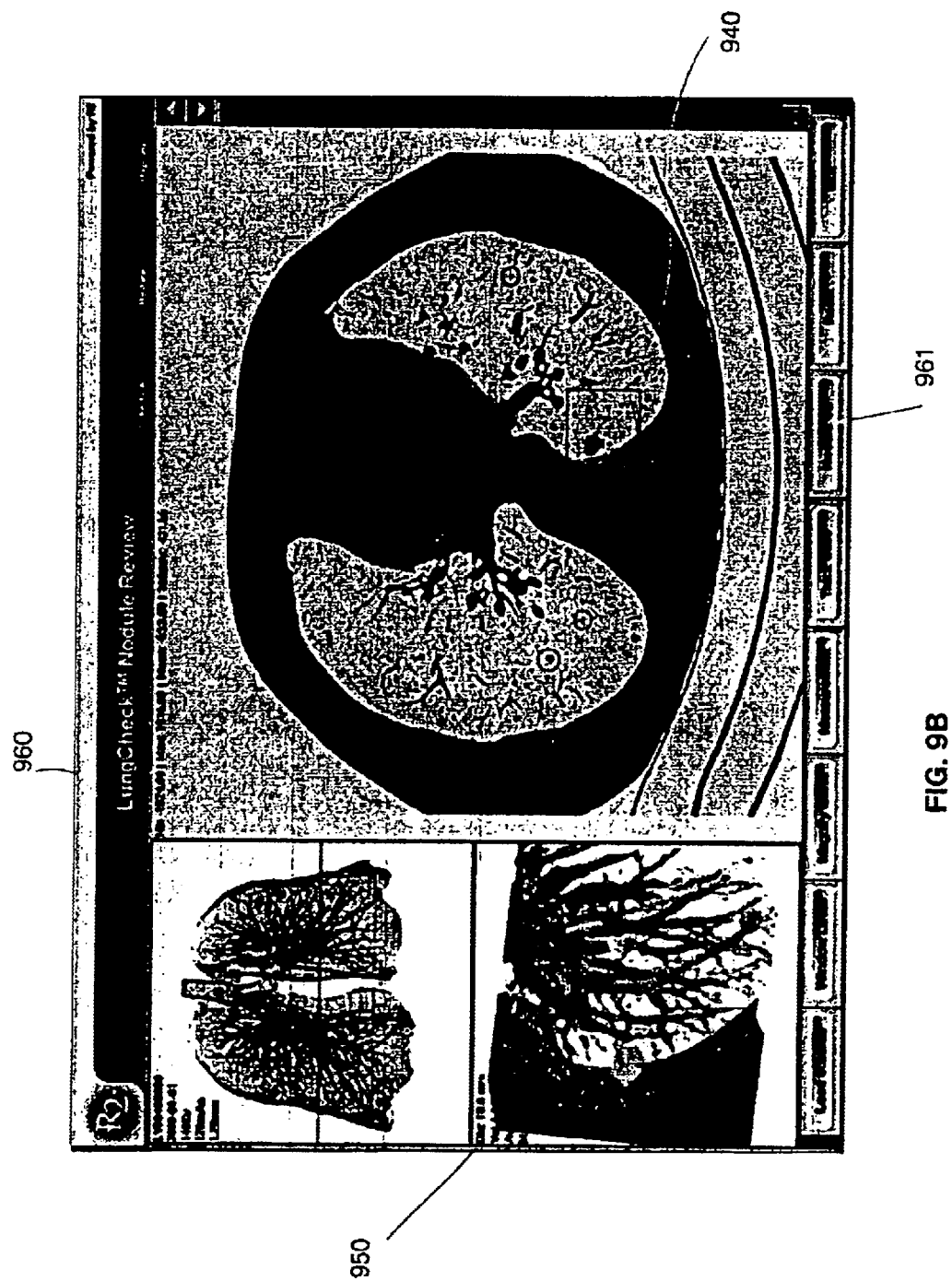
FIG. 9B is an illustration of a measurement feature that is activated upon clicking a fifth button on the display of FIG. 5.

Upon clicking on the measurement button 554, the left mouse button is activated. While the left mouse button is depressed, the computer system will display the radio opacity at the region of the CT section where the cursor is located. The measurement button can enable various other functionality. For example, a measurement function can be activated by a click-and-drag activation wherein the cursor can be placed in the first display 510, second display 520 or third display 530, and when the mouse is clicked and held, the cursor can be dragged within the display and a measurement calculated representing the distance covered by the cursor within the display. Additionally, the measurement can be automated. For example, in the third display 530, measurement data such as nodule diameter, volume, average intensity level and maximum intensity level can be displayed as data 950 (FIG. 9B) for a selected or highlighted nodule. The intensity level can be useful for determining whether a particular nodule is calcified or whether calcification occurred. Preferably, intensity levels are based on computed tomography numbers (CT numbers) expressed in terms of Hounsfield units (HU). Measured values of attenuation are transformed into CT numbers using the international Hounsfield scale:

$$\text{CT Number} = (\mu_{material} - \mu_{water})/\mu_{water} * 1000 \quad \text{(HU)}$$

where $\mu$ is the effective linear attenuation coefficient for the x-ray beam. The CT number scale is defined so that water has a value of 0 HU and air a value of minus 1000 HU.

As another example, intensity levels can be displayed in the third display 530 for a selected region 940. The intensity levels for the selected region may be displayed in the form of a histogram. Histogram information can be stored and used for statistical analysis for assessing whether calcification may be or has been occurring.

Figure 9C:
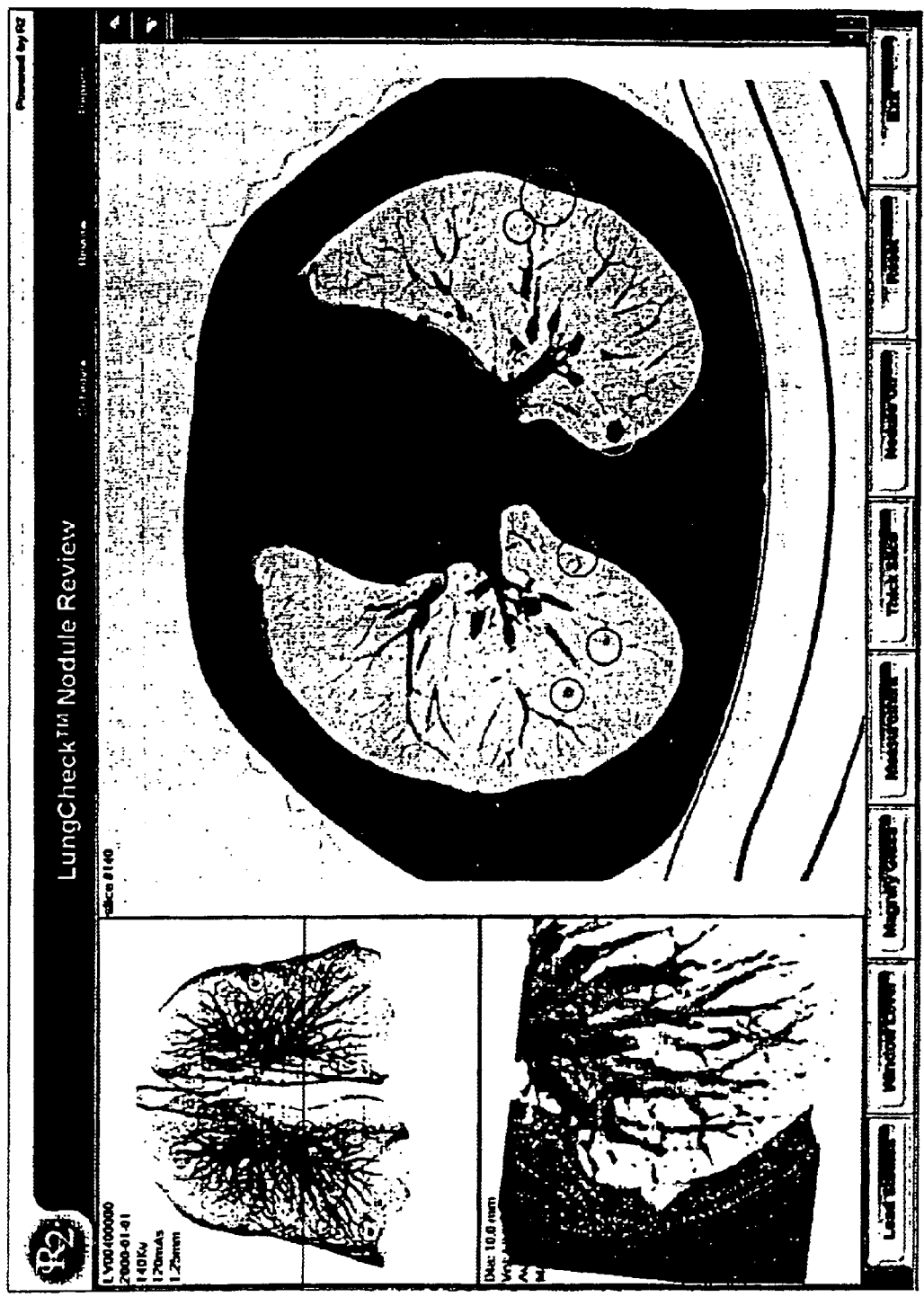
FIG. 9C is an illustration of the thick slice feature that is activated upon clicking a sixth button on the display of FIG. 5.

FIG. 9C depicts a representation when thick slice button 555 is activated. Images in a first display are composed of data from thicker slices or from CT scanners having multiple detectors. Thicker slices offer the advantage that non-linear effects of volume averaging (such as streaks) are reduced or eliminated as compared to conventional images formed at nominal slice thickness. Thicker slices offer faster computational and scanning times. Additionally, thicker slices are effective for screening programs. For such applications as screening, if the interface highlights nodules or other areas of concern, a patient can be re-scanned over the region of concern.

The nodule on button 556 toggles the nodule markers (e.g., white circles such as 541, 542, color coding or other devices to highlight individual nodules) on and off. Nodules can have circles of differing colors representative, for example, of whether a nodule has been considered, highlighted, or otherwise evaluated by a physician or other qualified personnel.

Figure 8:
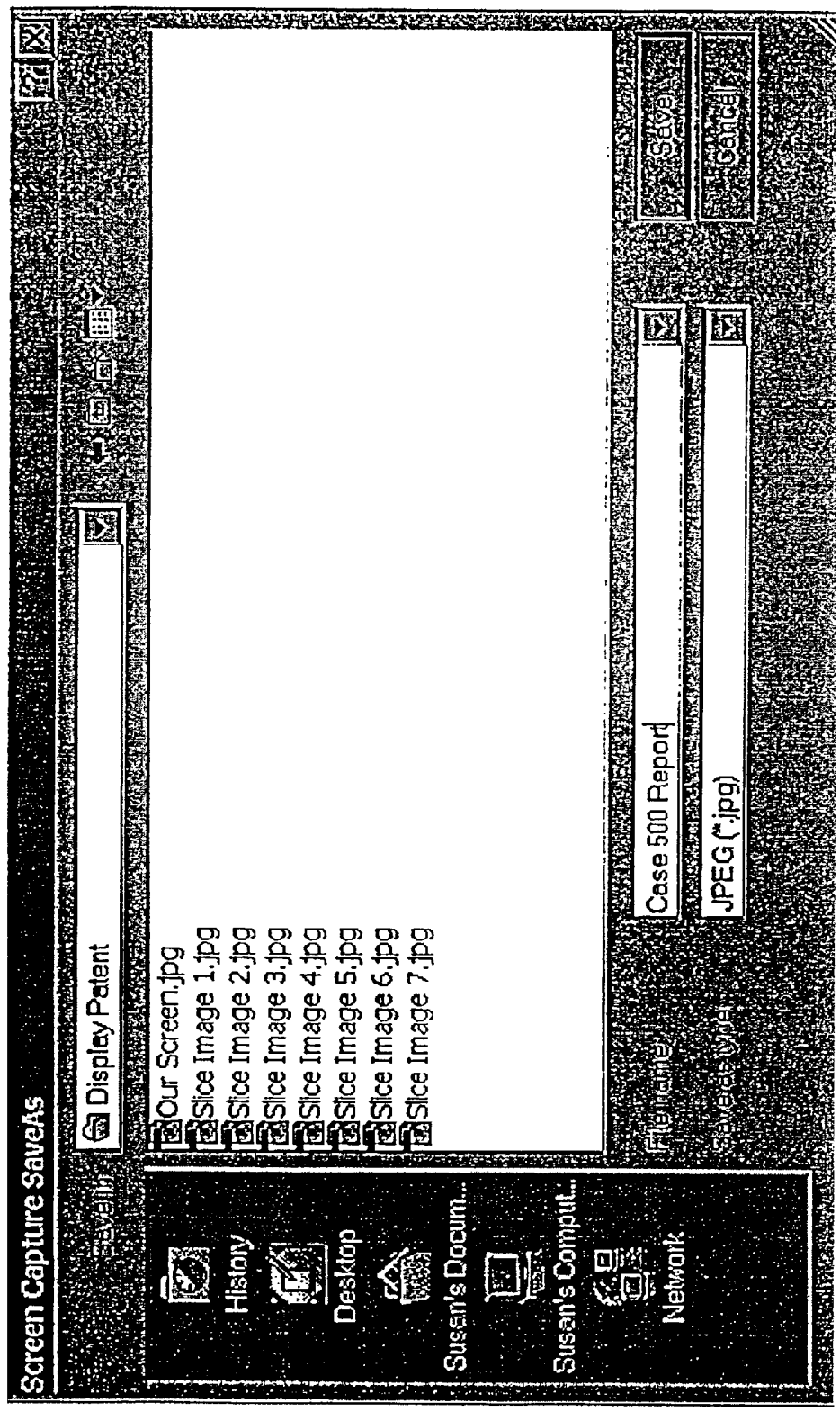

The reports button 563 captures the contents of the screen for direct input into a radiological report. Upon clicking on this button, the menu of FIG. 8 is displayed. This allows the user to select one of a variety of output options into which he or she can move the image on the display.

The reset button 557 resets all adjustments to the default values.

The exit button 558 terminates the program.

In one embodiment, a schedule button 561 provides a link to a pop-up window in which processing times can be scheduled. For example, in some cases it may be desirable to perform a CT scan but actually perform the nodule identification or other analysis at a later time. Delaying certain analysis can save patient time in running tests. In this way, screening of many patients can be done more quickly. Additionally, by scheduling batch processing at a later time, the interface can reduce or eliminate the need for any complex or time-consuming real-time or near real-time processing, particularly during screening or in the event the scanning procedure is operated by an individual not qualified to perform a diagnosis of the results. By storing pre-processed results from a scan, data can be processed at a later time. In this way, less patient time is required. Additionally, storing pre-processed results allows for scheduling processing time during down time while making results available for the evaluator in a timely manner.

Not shown in FIG. 5 but advantageously included in the array of function buttons is a configuration button that allows a user to select a variety of different display configurations. Upon clicking on the configuration button, a menu is displayed such as that depicted in FIG. 7. This menu includes a display 710, a scroll bar 712, and up and down buttons 714 and 716.

Figure 7:
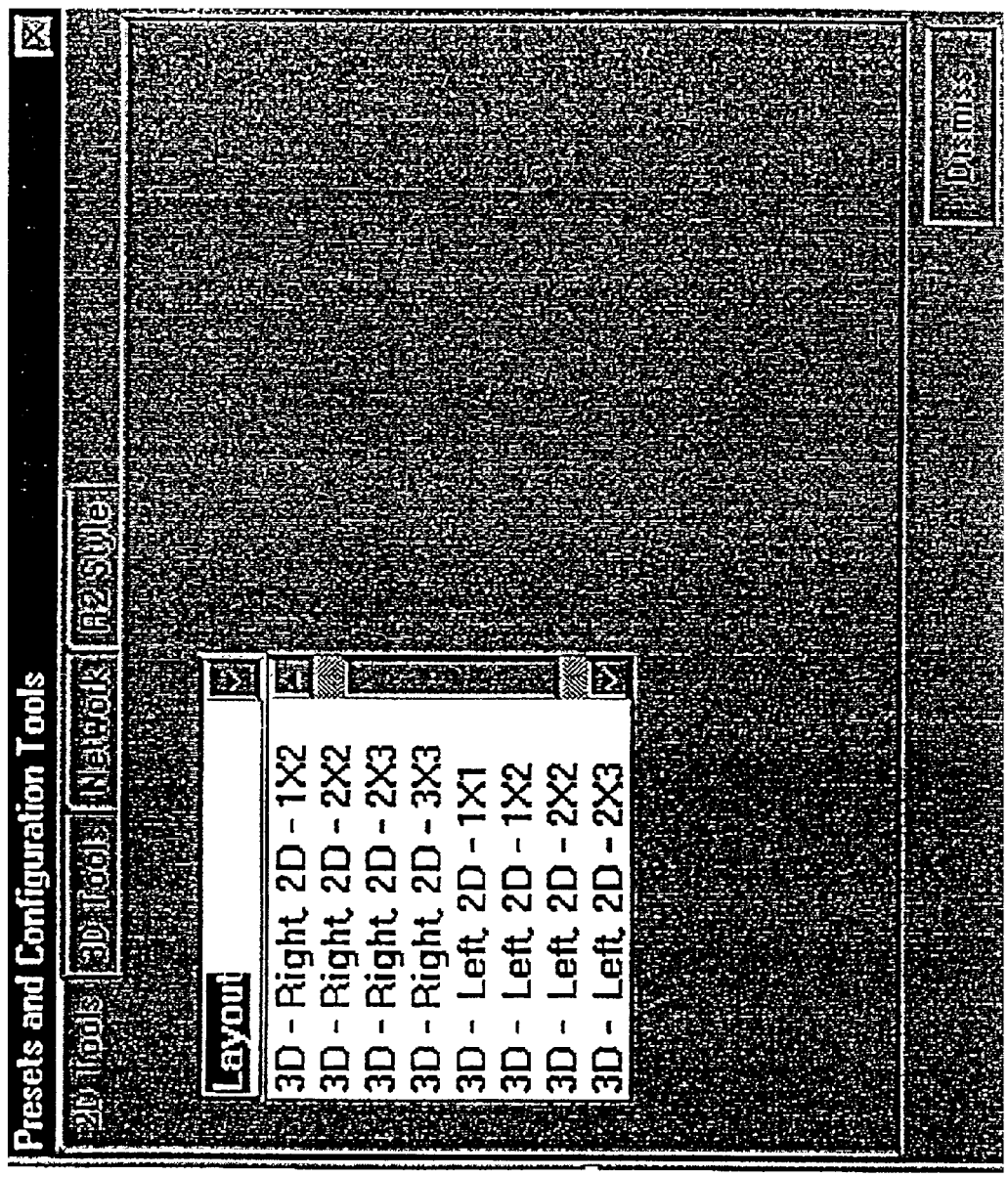

As shown in FIG. 7, display 710 allows selection of several different formats and more are available by use of the scrolling capability. The terms "3D-Right" and "3D-Left" allow the user to locate the second and third displays 520, 530 on the right-hand and left-hand sides, respectively, of the entire display. The terms "2D-1X1," "2D-1X2," "2D-2X2," "2D-2X3," and "2D-3X3" allow the user to select a single planar section, two sections, four sections, six sections or nine sections for display in first display 510.

Figure 10:
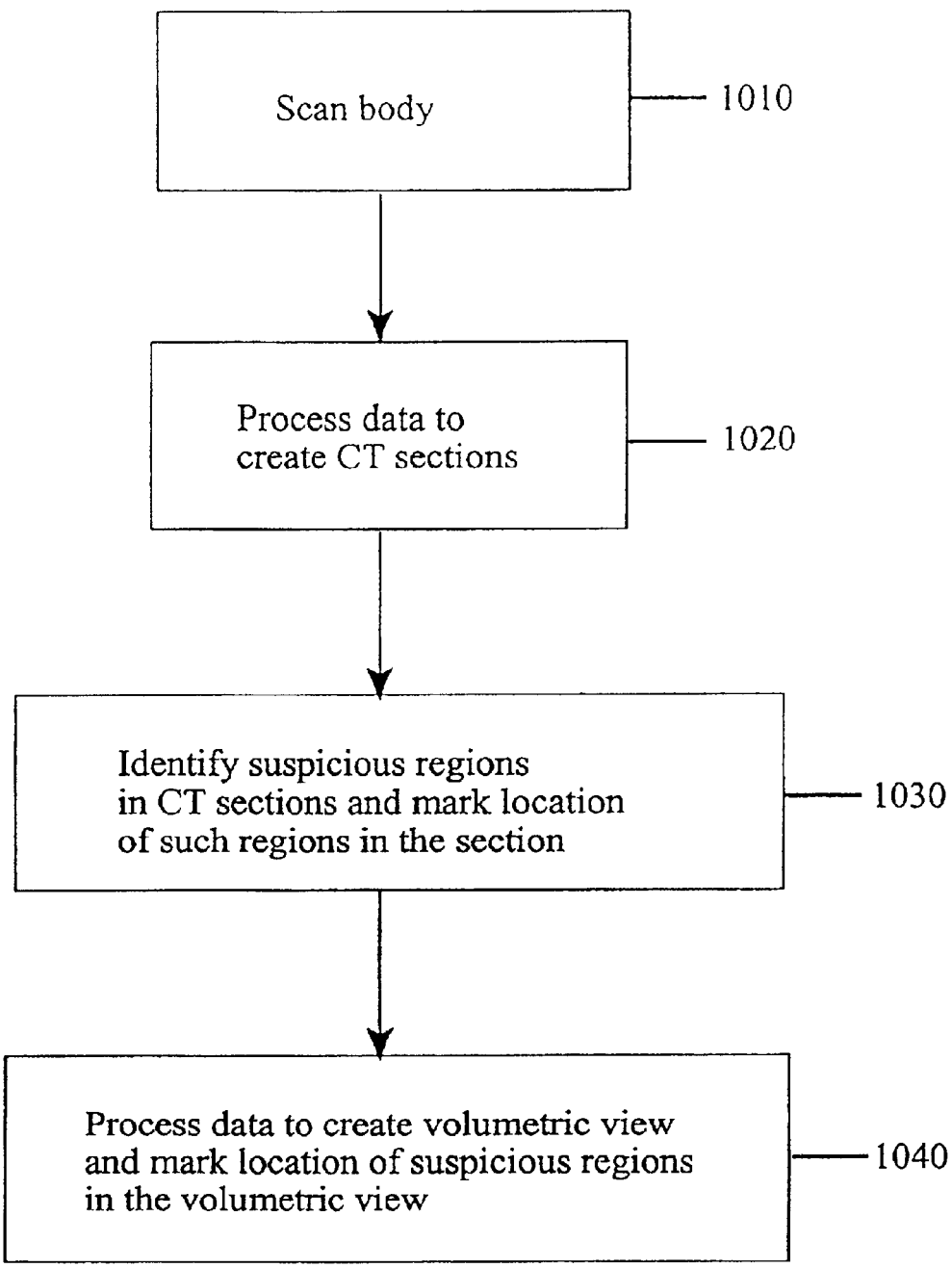
FIG. 10 is a block diagram illustrating the processing of CT data for use in the practice of the invention.
Figure 11A:
FIGS. 11A–11G are an illustrative series of CT sections that are displayed in a selected axial view (FIG. 5)
Figure 11B:
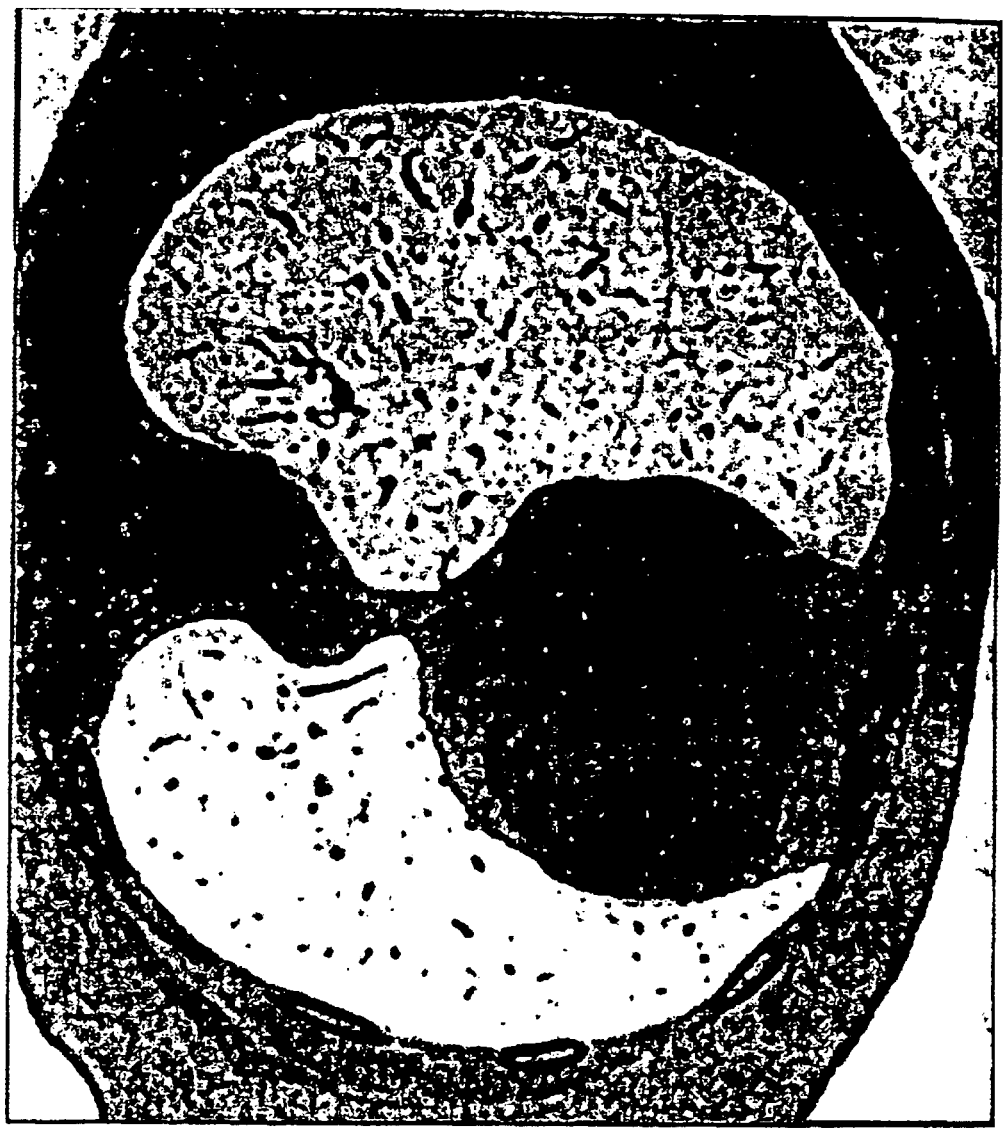
Figure 11C:
Figure 11D:
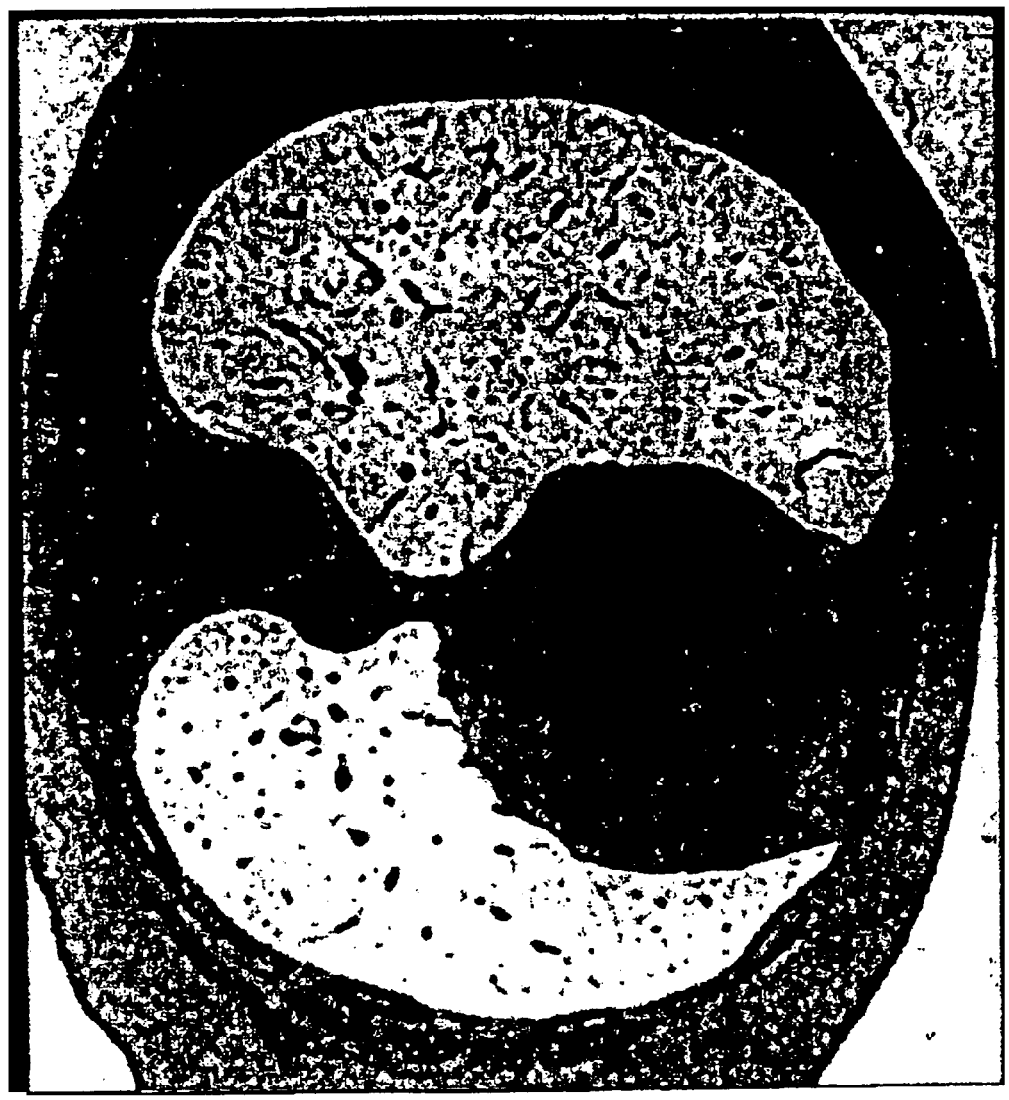
Figure 11E:
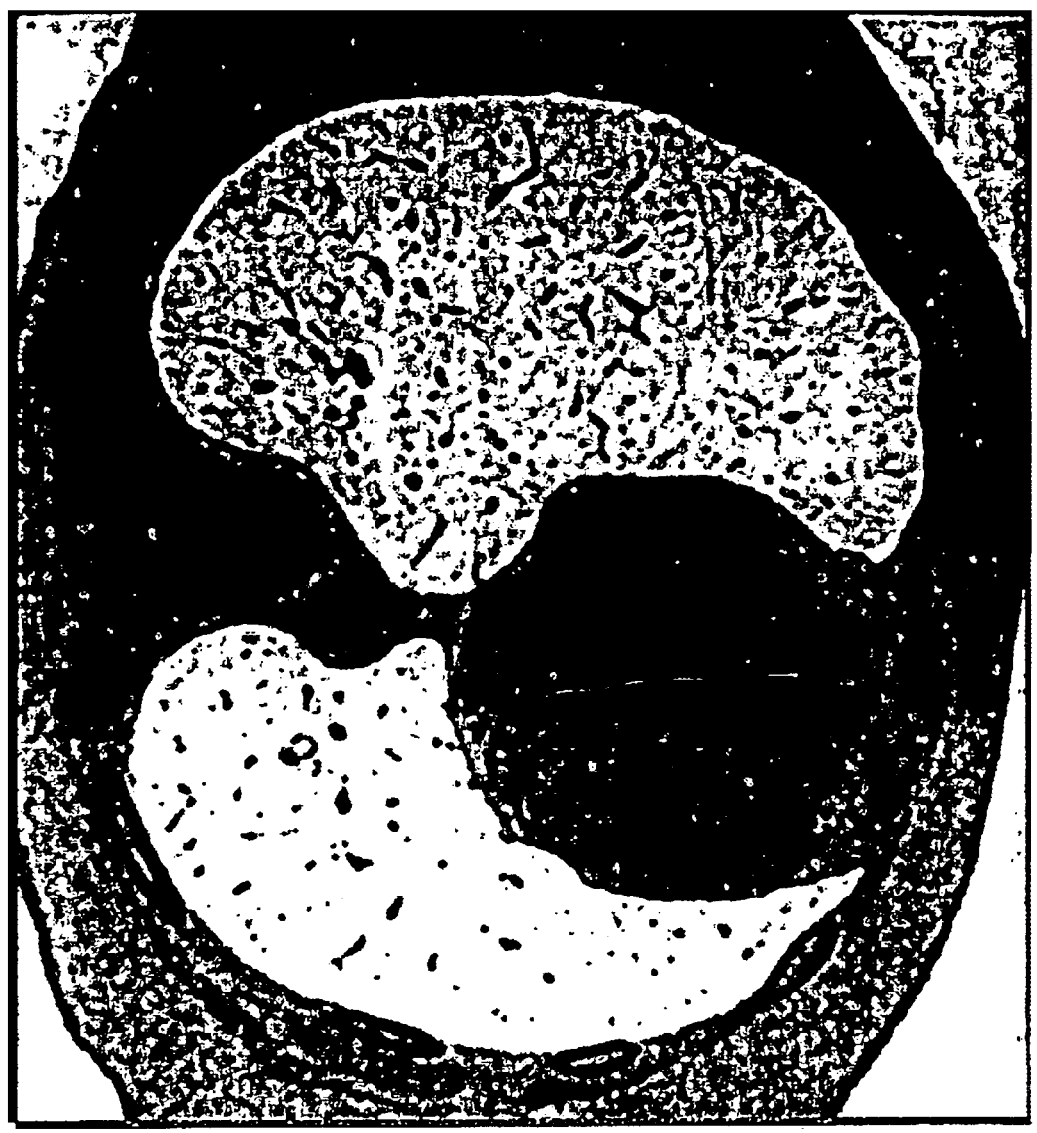
Figure 11F:
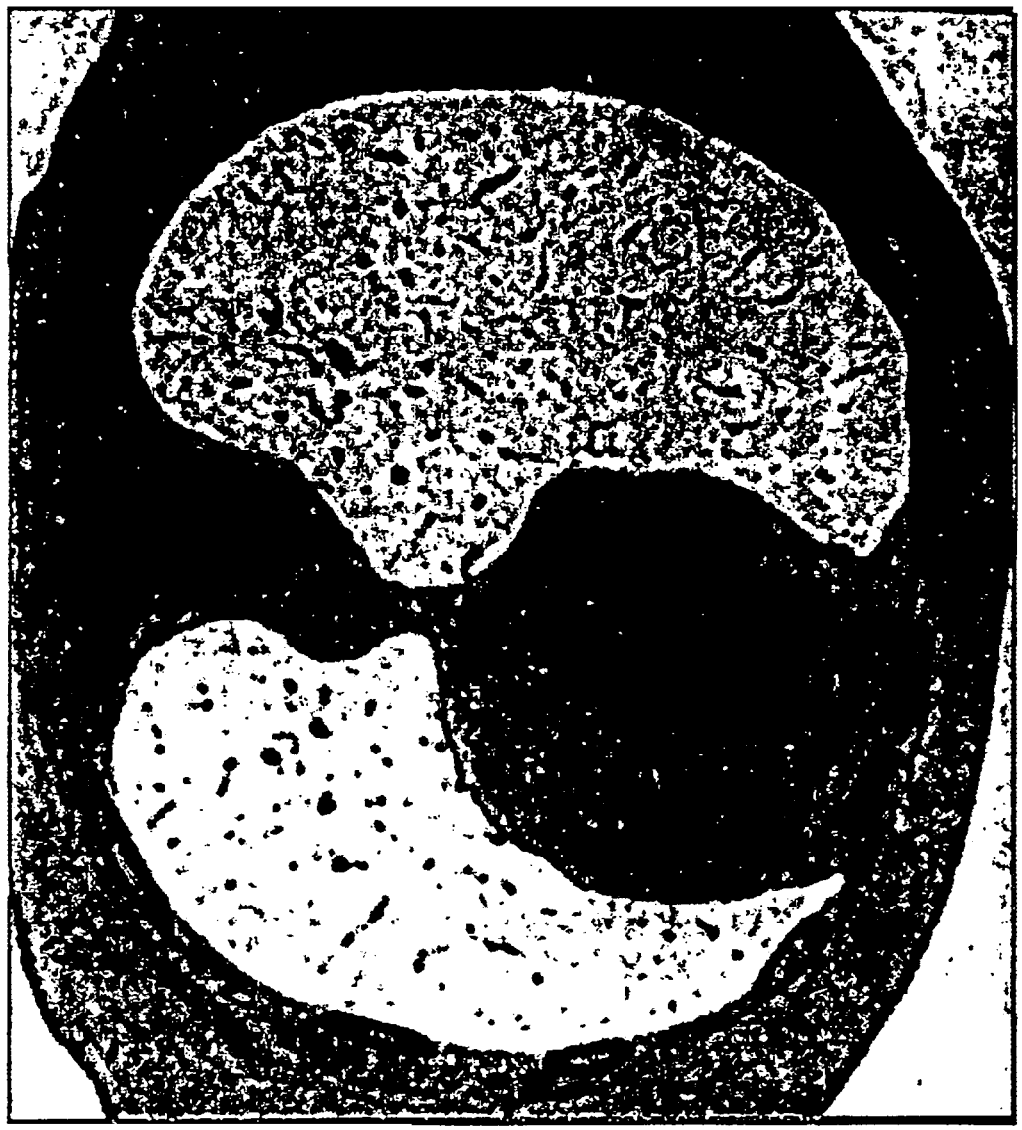
Figure 11G:
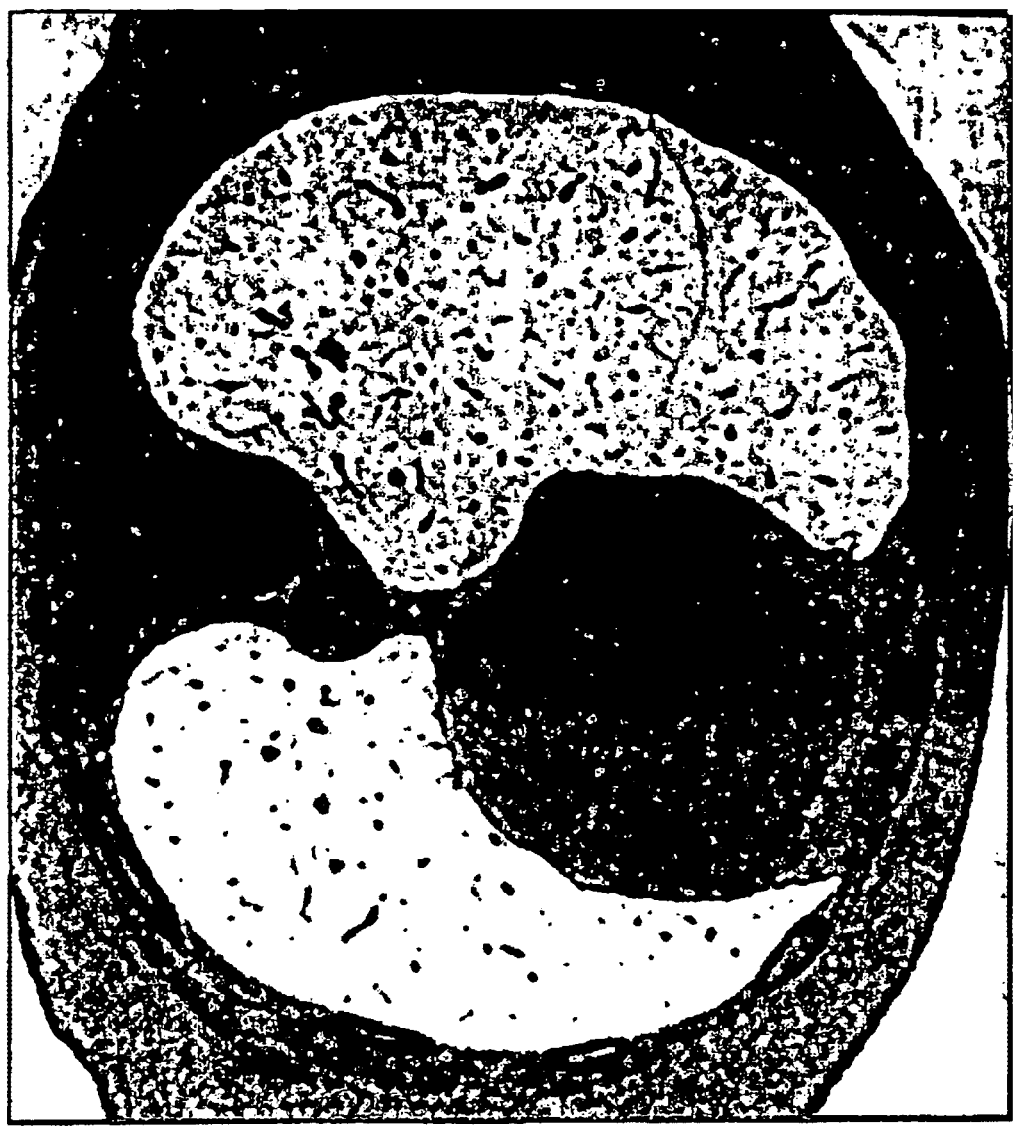
Figure 12A:
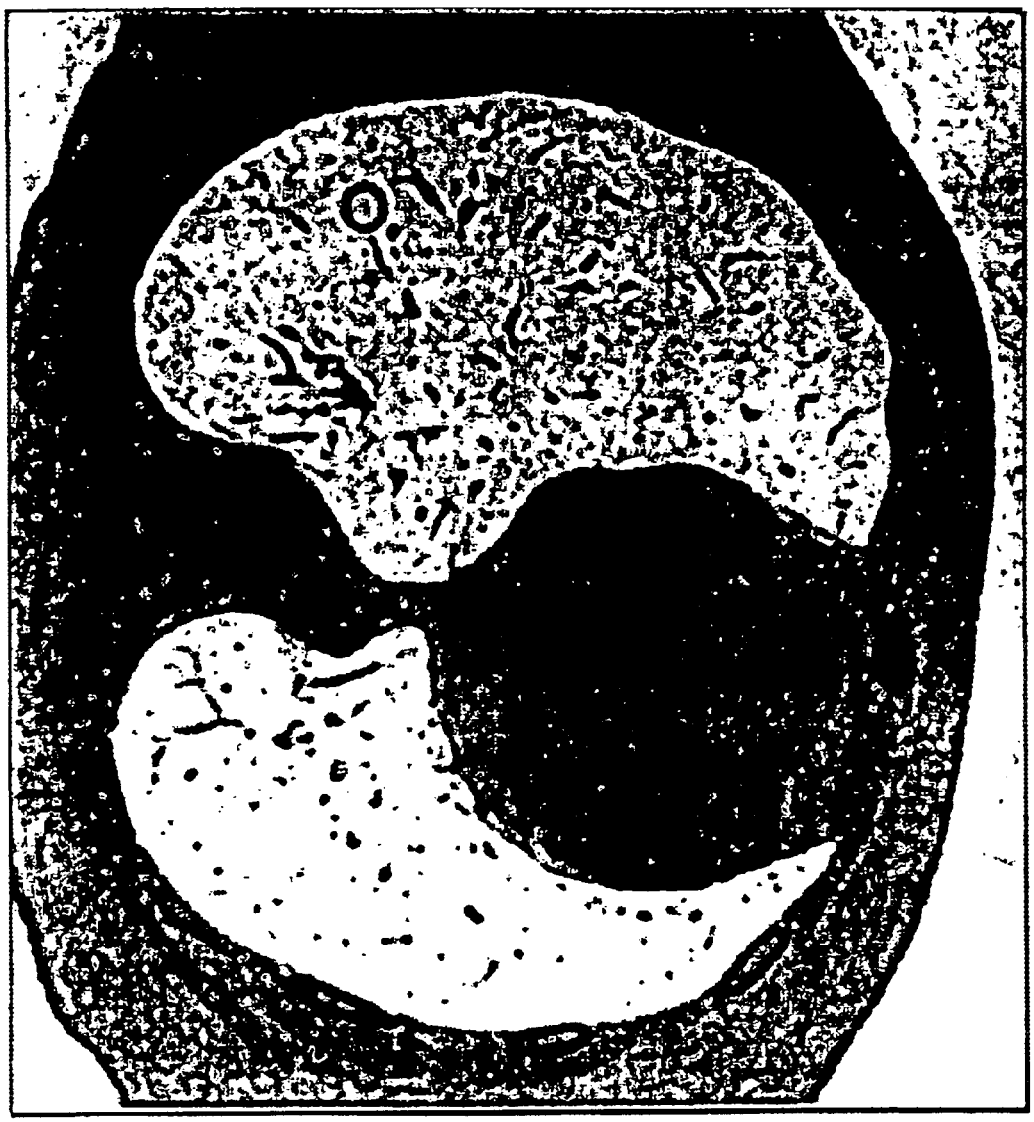
FIGS. 12A–12G are the same series of CT sections as in FIGS. 11A–11G but with a potentially cancerous nodule marked in accordance with the invention.
Figure 12B:
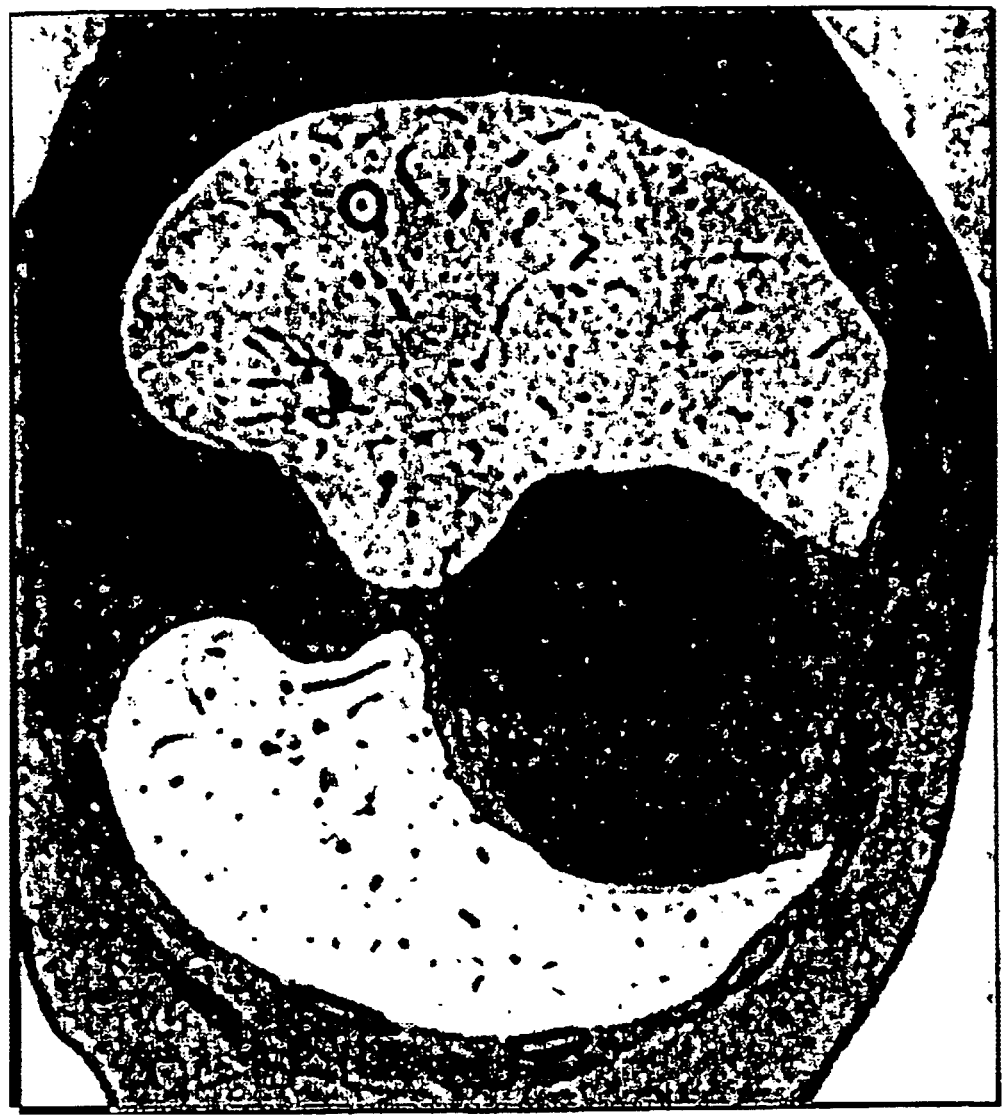
Figure 12C:
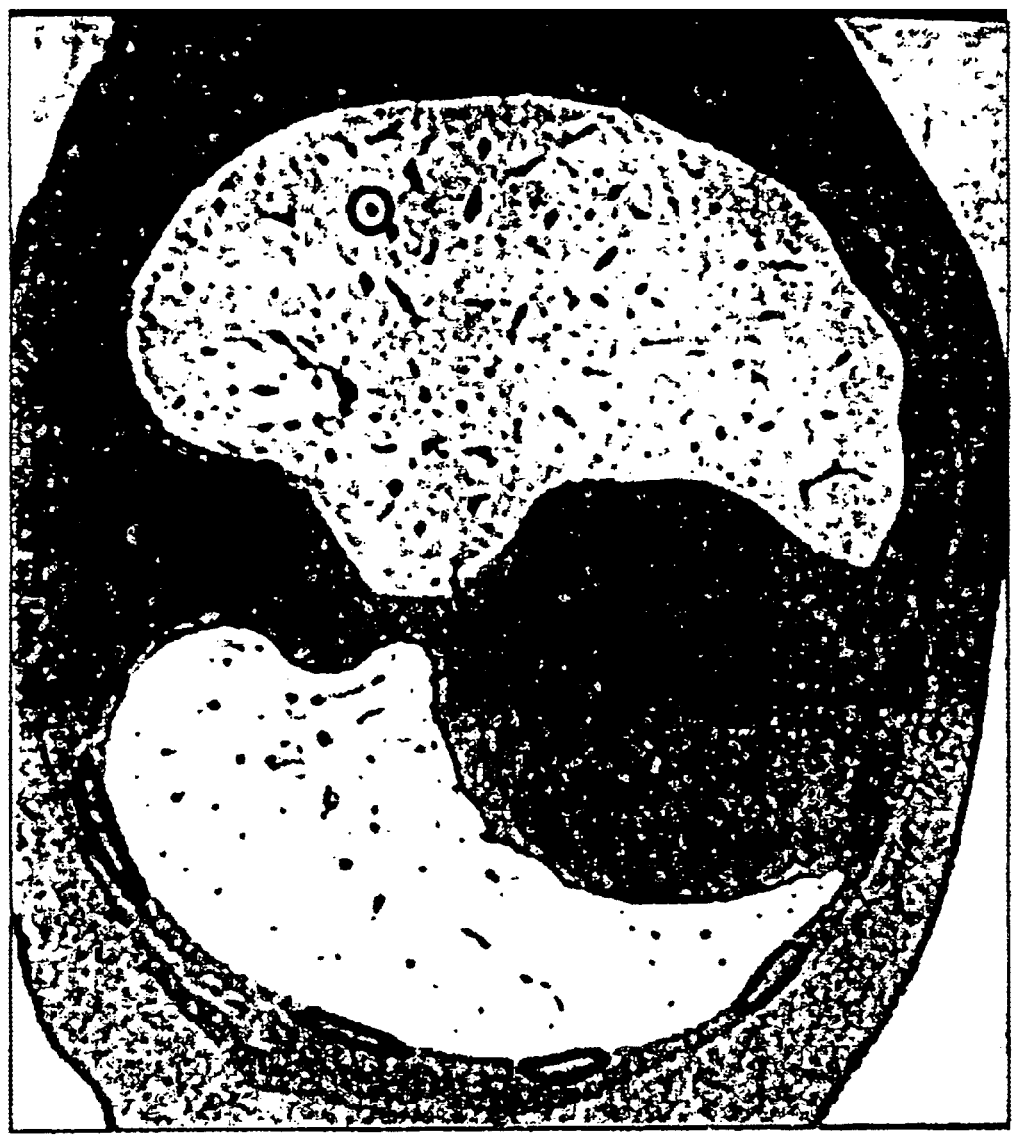
Figure 12D:
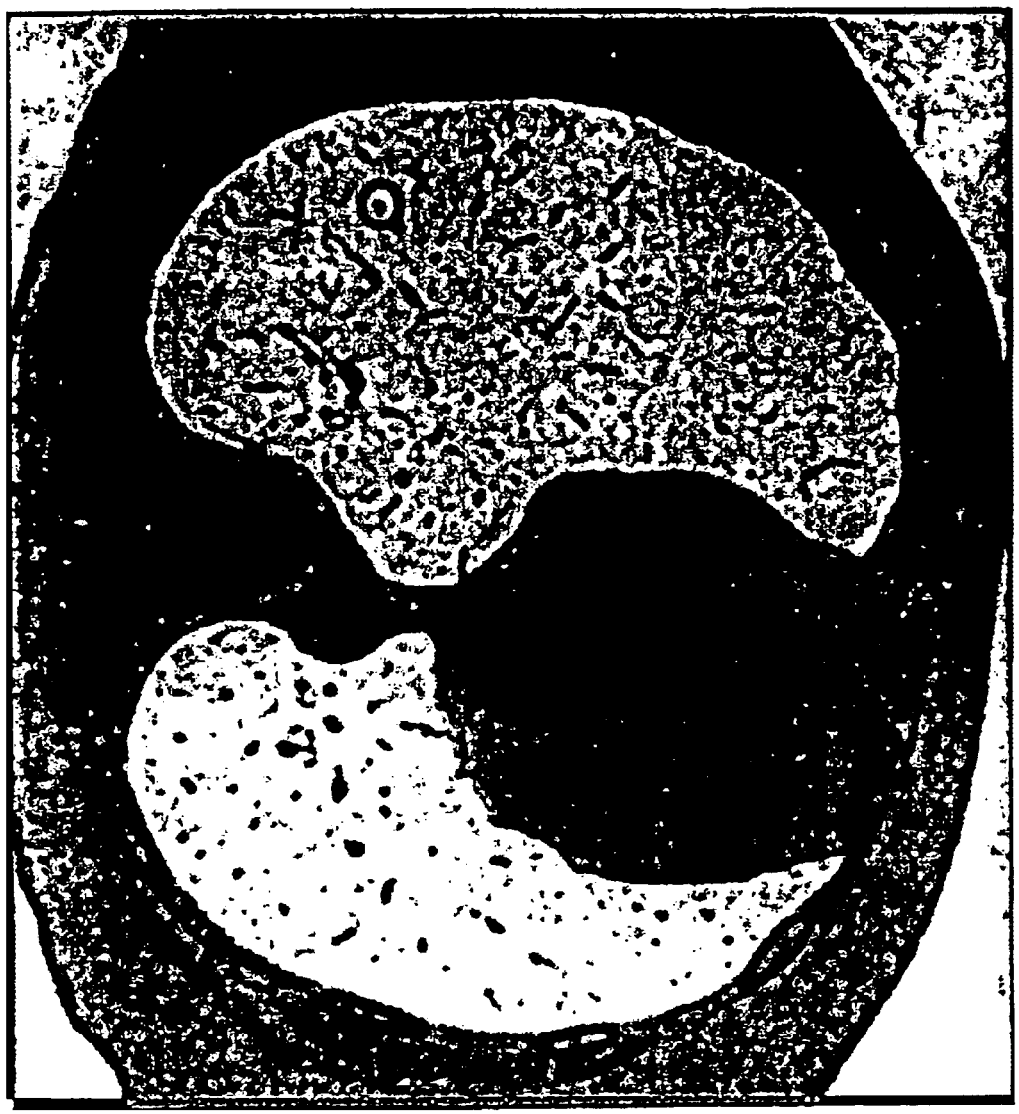
Figure 12E:
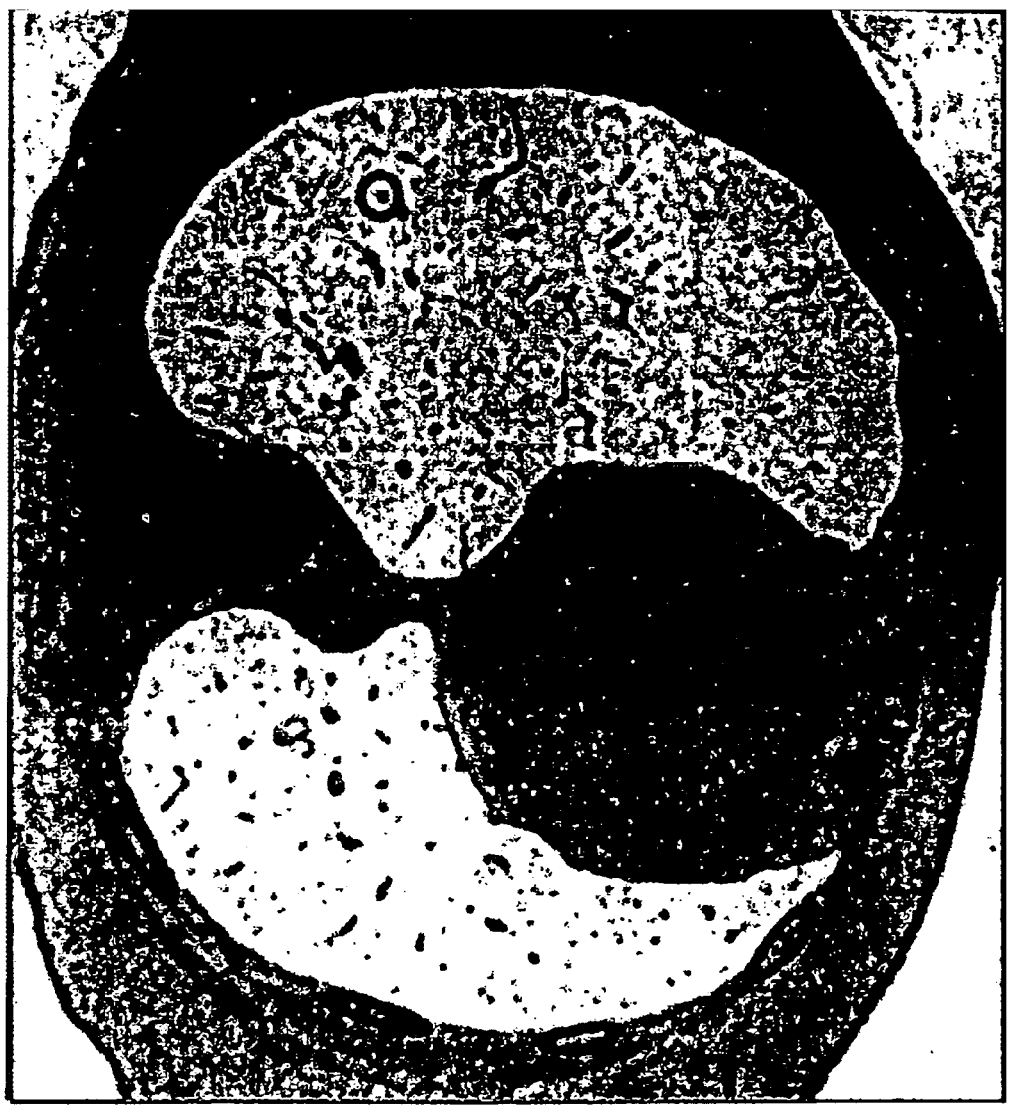
Figure 12F:
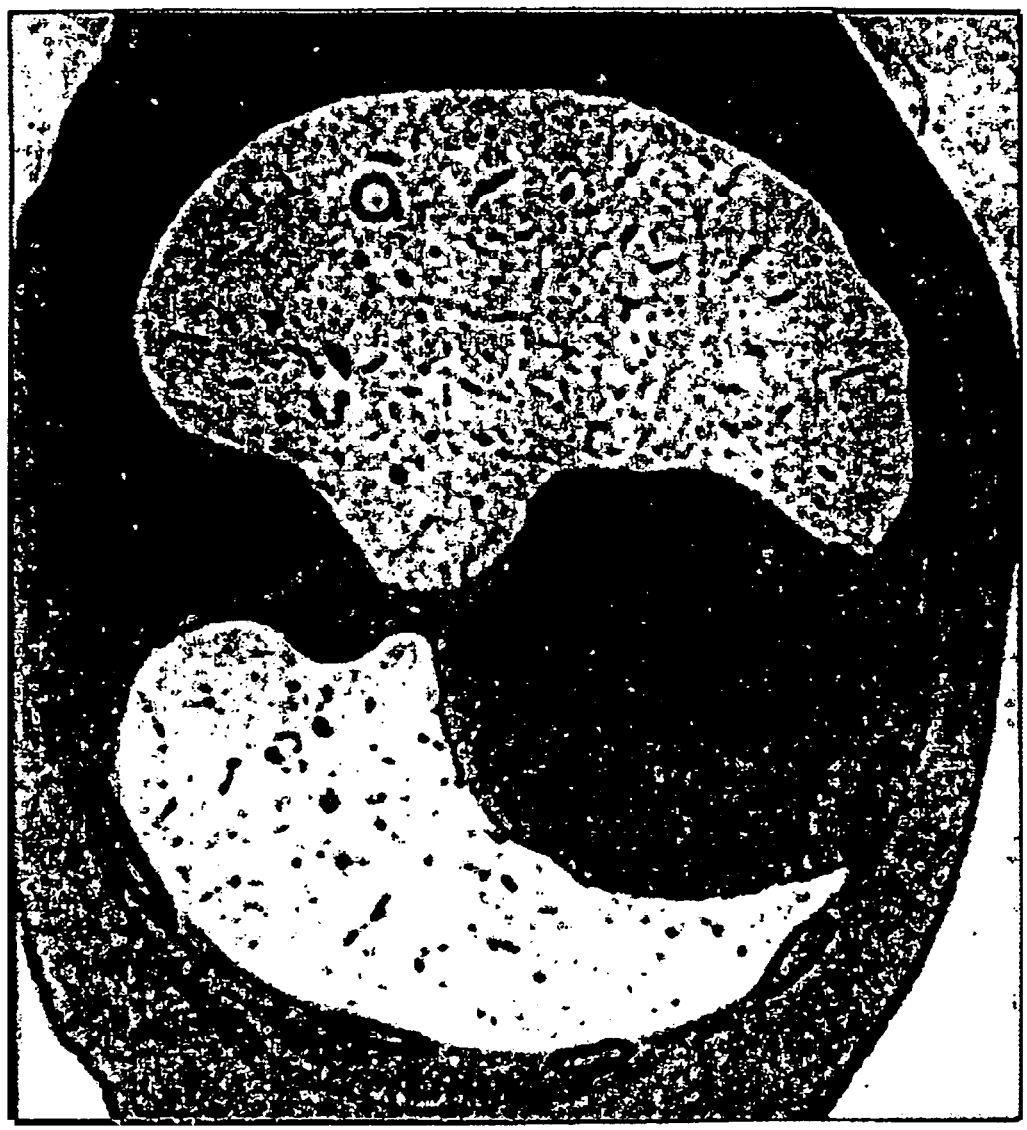
Figure 12G:
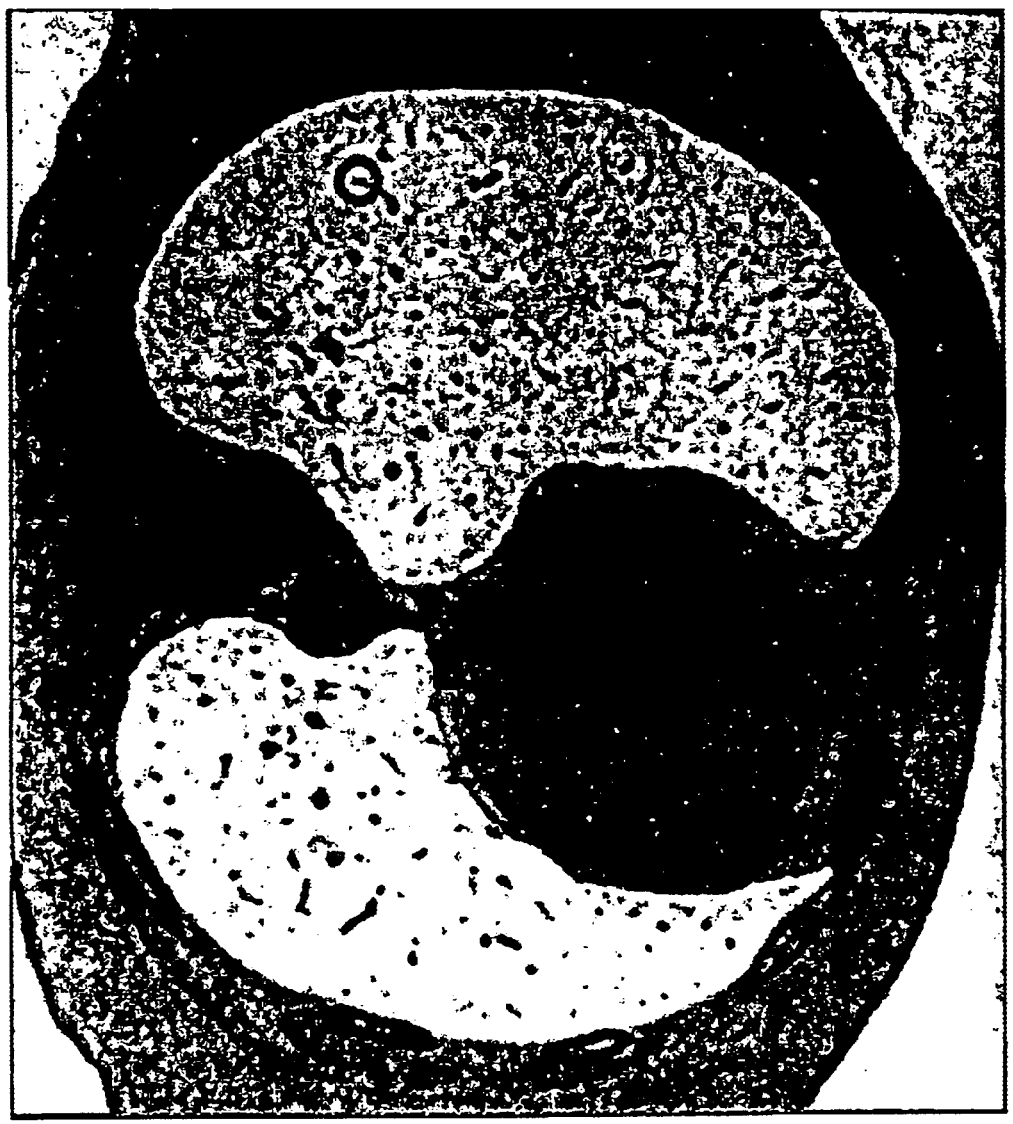

FIG. 10 is a block diagram illustrating the processing of CT for use in the practice of the invention. At step 1010, conventional CT apparatus scans the portion of a patient's body. At step 1020, the signals produced from the detectors of the CT apparatus are processed to generate CT planar sections. Illustratively, each section is identified by a slice number, a patient identification number and a time stamp. At step 1030, the planar sections are further processed to identify and mark suspicious regions on the planar sections. These regions are referred to hereinafter as regions of interest (ROI). The regions are detected using segmentation and image filtering algorithms similar to those described in U.S. Pat. Nos. 6,014,452, 5,815,591 and 6,075,879 assigned to R2 Technology, Inc. Where the CT sections are being examined to detect lung cancer, the algorithms are optimized to locate nodules between 2 and 20 mm. in the parenchymal regions of the lung, and as small as 1 mm for small calcified nodules, calcification being a diagnostic indicator for benignancy. Advantageously, the sections containing ROI are noted by slice number and a vector of slice numbers is generated identifying the section through the center of each ROI. As described below in conjunction with FIG. 16, this vector is used to navigate through the display of ROI. Finally, at step 1040, the data is further processed to create a volumetric view of the region encompassed by the CT sections and to mark the location of the ROI on this volumetric view. At present, the processing depicted in FIG. 10 is done off-line on a computer different from that of the computer of FIG. 3 on which the axial and volumetric displays are generated.

FIGS. 11A–11G are an illustrative series of seven consecutive CT axial sections as they would be seen in the first display 510 with the nodule marker toggled off. There is a potentially cancerous nodule in the upper left quadrant of these sections. The difficulty of detecting the nodule will be apparent.

FIGS. 12A–12G are the same series of seven consecutive CT axial sections but now displayed with the nodule marker toggled on and a white circle circumscribing the potentially cancerous nodule.

Figure 13:
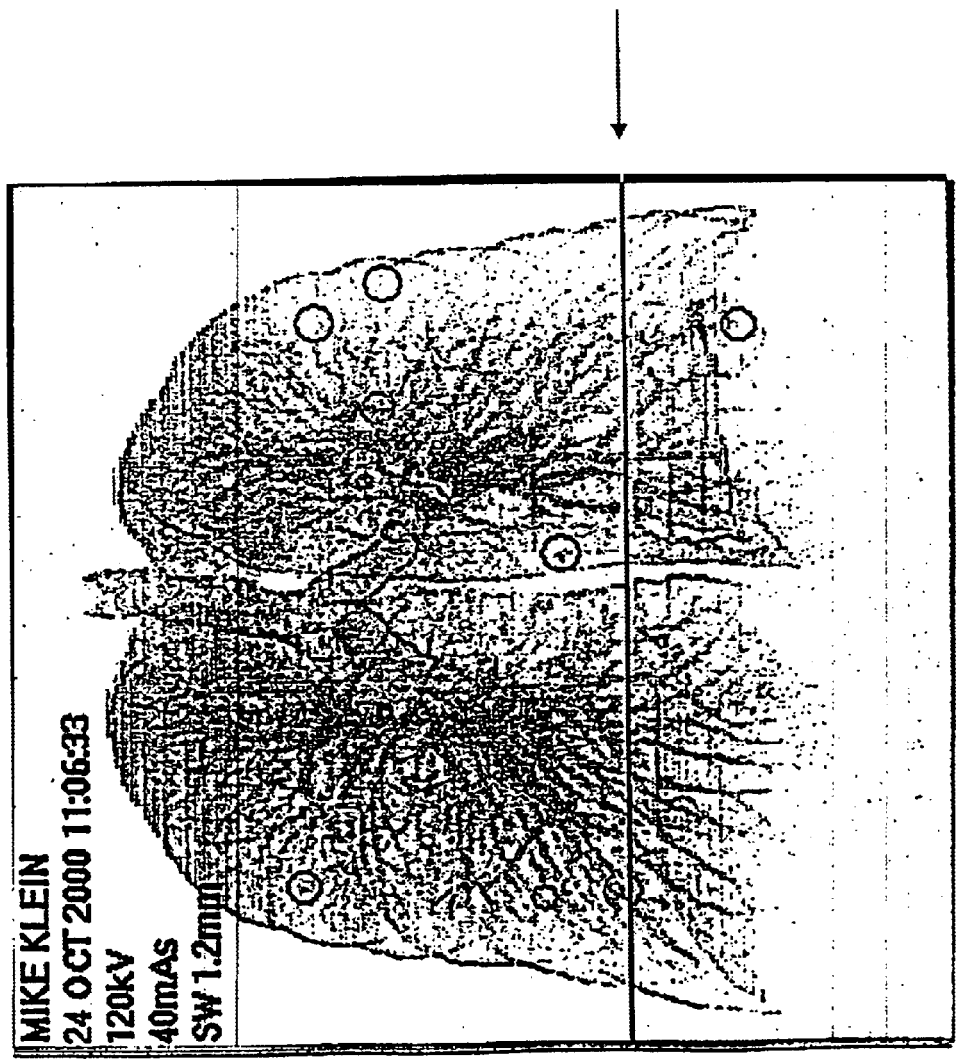
FIG. 13 is an illustrative view seen in a second portion of the display of FIG. 5.

FIG. 13 is an enlarged view of the volumetric display in the second display 520. Each ROI in the CT sections is indicated by a circle at its corresponding location in the volumetric display. The white horizontal line indicates the location in the volumetric display of the axial section then being displayed in first display 510.

Figure 14:
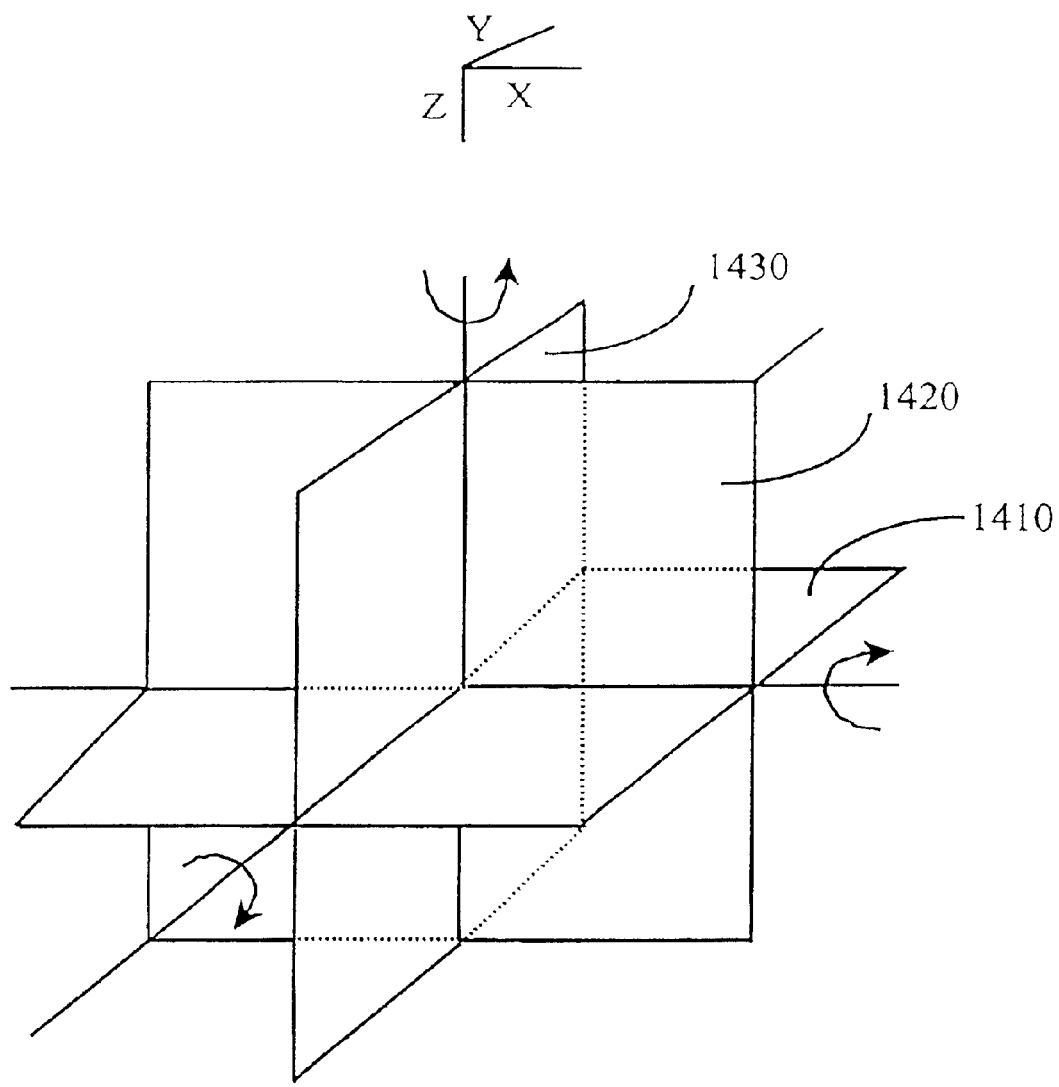
FIG. 14 is a sketch useful in understanding FIGS. 15A–15D.

FIG. 14 is a sketch useful in understanding display 530. FIG. 14 depicts a horizontal plane 1410 and two vertical planes 1420 and 1430 at right angles to each other. The X, Y and Z directions are as indicated. The axial sections of display 510 lie in the horizontal plane 1410. In accordance with the invention, trackball 350 or mouse 360 can be used to rotate the viewpoint in display 530 about at least two axes, typically the vertical axis and one or both of the horizontal axes.

FIGS. 15A–15D depict four views of the same ROI at different rotations. The cancerous nodule is circumscribed by a white circle. As will be apparent, the ability to rotate the viewpoint makes it possible to establish that the mass shown in the viewpoint of FIG. 15D as possibly connected to other structures is, in fact, isolated therefrom as shown in the viewpoints of FIGS. 15A–15C and therefore suspicious.

Advantageously, a set of reference symbols is provided in each display to orient the user. The direction of view in FIG. 15D is the same as that in display 520, that is, into the plane of the axial section. This is depicted in the reference symbol of FIG. 15D by showing the full extension of the X coordinate in a horizontal line and the full extension of the Z coordinate in the vertical direction. The direction of view in FIG. 15C is downward through the axial section with about 5° of clockwise rotation about the Z axis and a small amount of rotation of the axial section about the X axis. This is depicted in the reference symbol of FIG. 15C by showing the X and Y coordinates as they would be seen looking down through the axial section with the Y coordinate shorter than the X coordinates and the X and Y coordinates rotated about 5° clockwise. The direction of view of FIGS. 15A and B are upwards through the axial sections. This is depicted in the reference symbols of FIGS. 15A and 15B by showing the X and Y coordinates in the orientation they would have if looking upward through the CT section. In FIGS. 15A and 15B the views have also been rotated about the Z axis but in opposite directions. In addition, the views have been rotated about one or both of the X and Y axes as suggested by the extension of the Z coordinate.

Also displayed in the views of FIGS. 15A–15D are measurement data of the volume and diameter of the ROI. Once the ROI is identified, the volume of the ROI can be determined by the computer system by counting the voxels in the ROI. The resulting volume is then converted to a diameter by assuming the volume is a sphere and using the standard formula for relating the diameter of a sphere to its volume.

Figure 16:
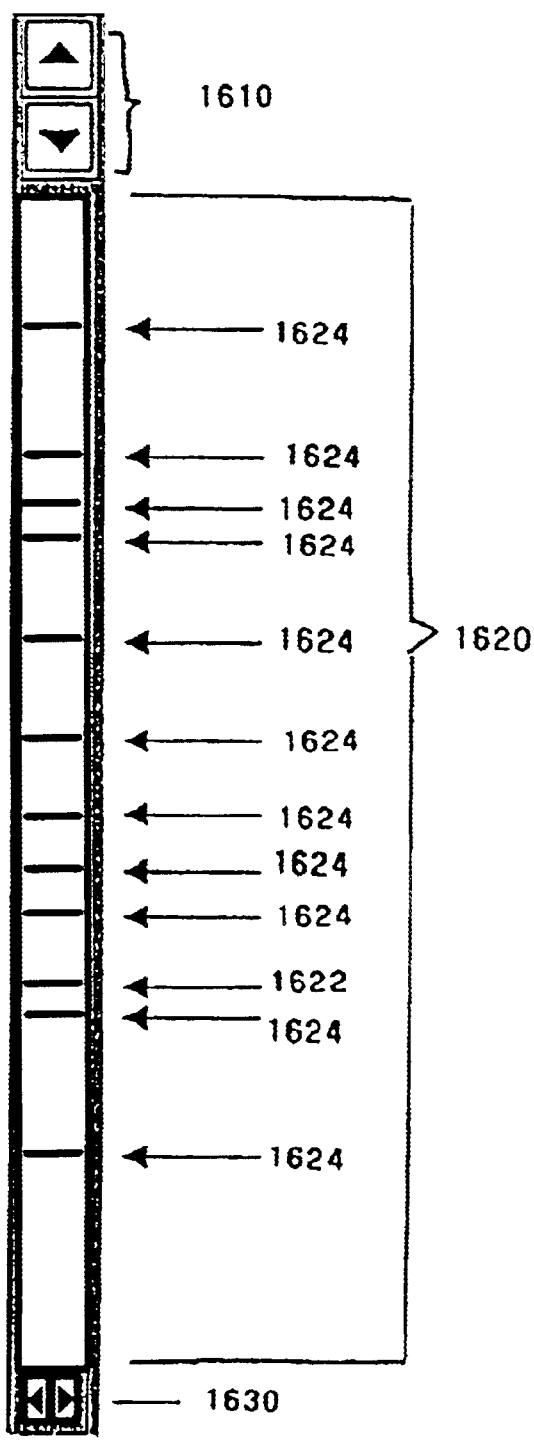
FIG. 16 is an illustrative view of a scrolling control for the display of FIG. 5.

FIG. 16 is an enlarged view of navigator or scroll bar 540 of FIG. 5. The lesion or nodule navigator comprises a first set of up and down scroll buttons 1610, a display bar 1620, and a second set of left and right scroll buttons 1630. Display bar 1620 is a visual display of the vector of slice numbers that contain a ROI. Each slice number in the vector is represented in the display by a horizontal line. The horizontal line is an identifier of CT sections that are determined to contain at least one nodule. The CT section then being displayed in display 510 is indicated by an identifier, such as white line 1622 in FIG. 16. The other CT sections are indicated by other identifiers, such as dark lines 1624. The lines are spaced apart by an amount proportional to their distance from each other in the complete case of CT sections.

The navigator scroll buttons 1610 enable the user to step the display of CT sections in display 510 from one section containing a ROI to another section containing a different ROI. Specifically, with each click of an up or down scroll button 1610, display 510 goes from the display of a CT section containing a ROI to the display of the CT section containing the next ROI.

As indicated above, a horizontal line extends across volumetric display 520 indicating the location of the axial section then being displayed in display 510. As the navigator scroll buttons 1610 change the CT section being displayed, the location of the white horizontal line 1622 on display 1620 and the location of the white horizontal line on volumetric display 520 change accordingly.

Likewise, the magnified view on display 530 changes to the ROI identified on the selected CT section.

Left and right scroll buttons 1630 enable the user to navigate through the entire case of CT sections one-at-a-time. Each click of a button changes the display to the next section in the case. These buttons provide more precise CT viewing around the identified ROI. Advantageously, a scroll bar (not shown) may also be provided to allow the user to scan through the sections at a speed controlled by movement of the scroll bar.

Figure 17:
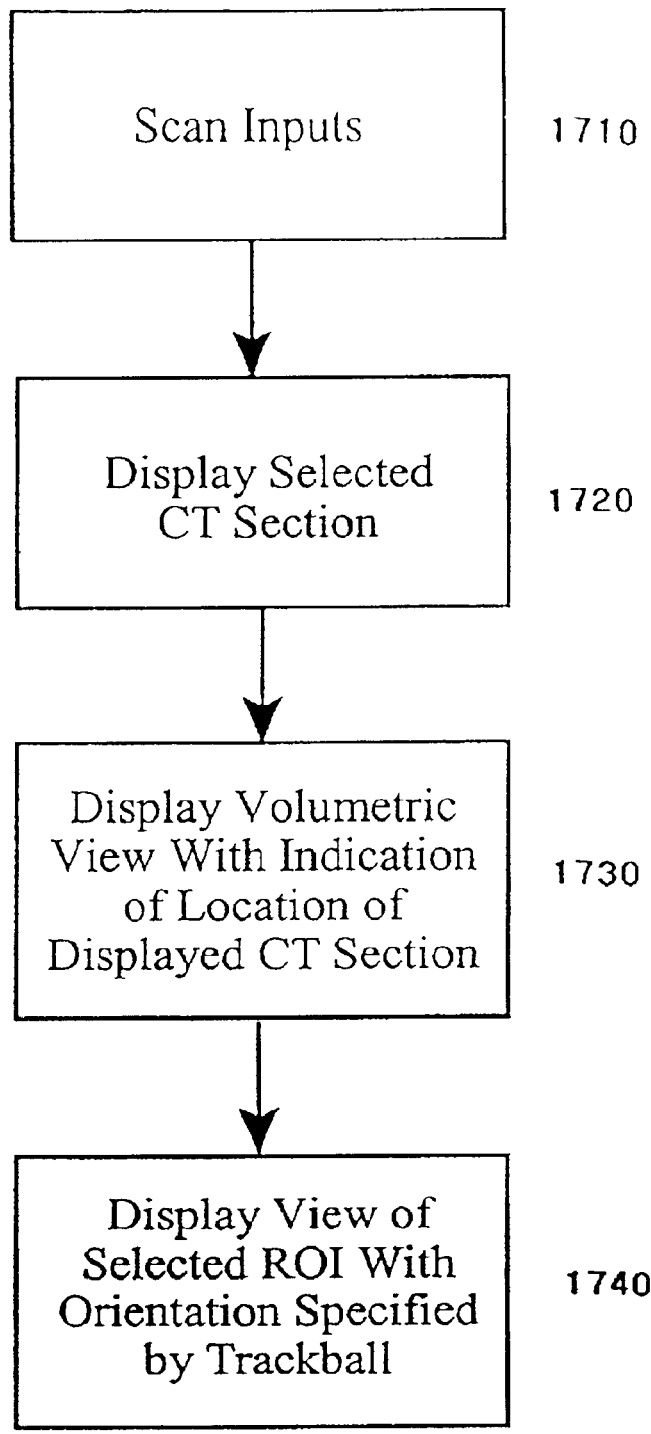
FIG. 17 is a block diagram illustrating the operation of a preferred embodiment of the invention to display CT data.

FIG. 17 is a block diagram illustrating the operation of the computer system 300 to display CT data in accordance with the invention. At step 1710, the computer system scans the inputs to the system. These include the status of the trackball 350 and mouse 360, the status of navigator 540, and the status of the function buttons of array 550. Specifically, the white horizontal line 1622 determines the CT section to be displayed on display 510, the location of the horizontal line on display 520 and the ROI displayed on display 530. The inputs from trackball 350 or mouse 360 control the orientation of display 530 and inputs from the function buttons control the display of various menus and the execution of other operations.

Assuming that the operation to be performed is display of an CT section, the computer system displays the selected section at step 1720. It also displays at step 1730 the volumetric view of display 520 with a horizontal line indicating the position of the axial section; and it displays at step 1740 the view of the ROI on display 530 with an orientation specified by the inputs from the trackball or mouse.

Figure 18:
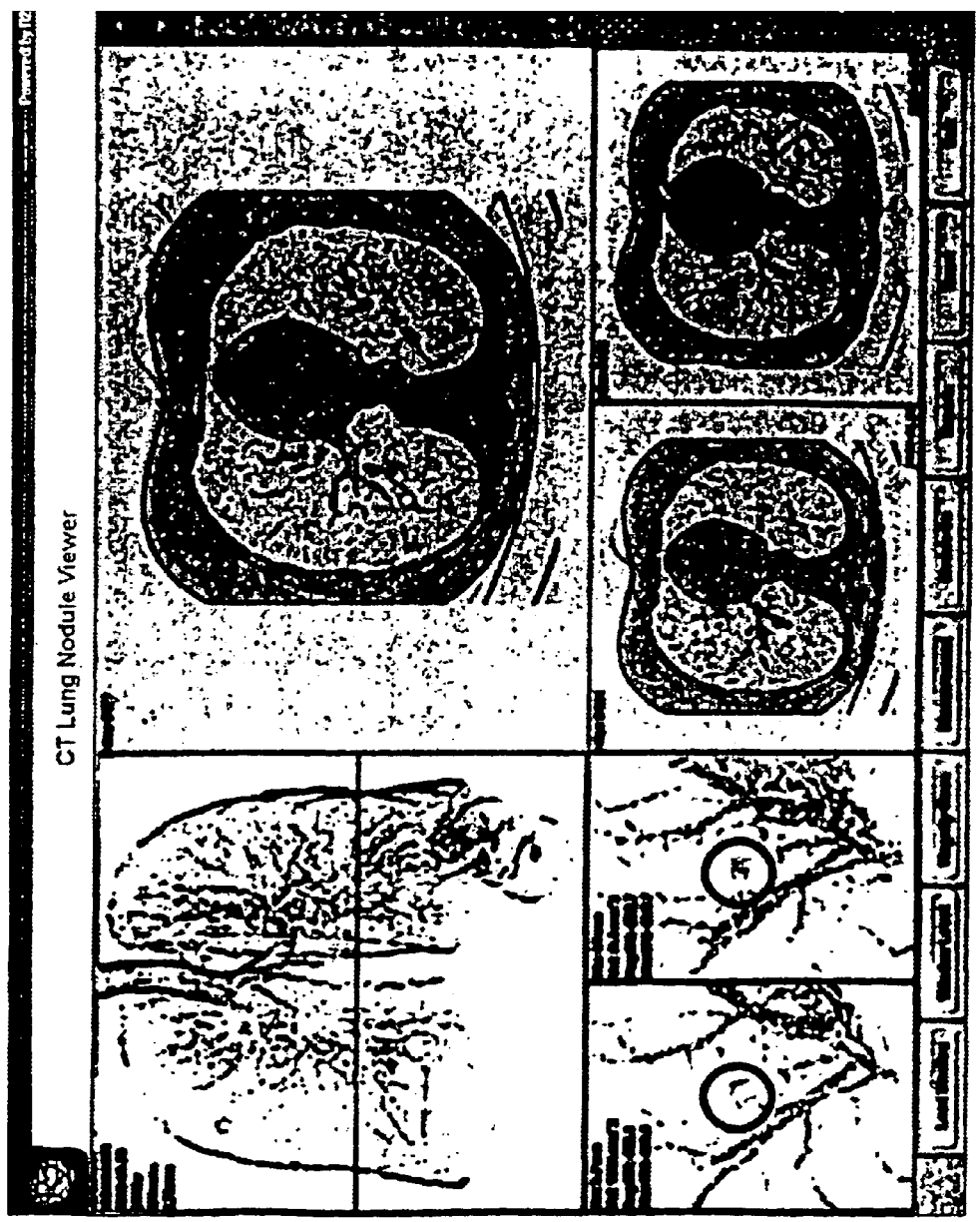
FIG. 18 is an illustration of a second computer display of the present invention that provides for display of temporal data.

FIG. 18 is a view of second embodiment of the display that provides for the display of temporal information. The top portion of the display is similar to that of FIG. 5. The bottom part provides on the right-hand side a smaller view of the axial section immediately above it and a view of a similar axial section taken at a previous time. On the left-hand side, two magnified volumetric views are shown, one that corresponds to the ROI identified on the CT section displayed in the upper right-hand portion of the display and the other corresponding to the same ROI as imaged at a previous time. By presenting views taken at different times, the physician is able to assess any changes that have taken place in the ROI. Volumetric change over time is an indicator of malignancy of an identified nodule. At the bottom of the display is a series of function buttons similar to those of the display of FIG. 5.

Figure 19:
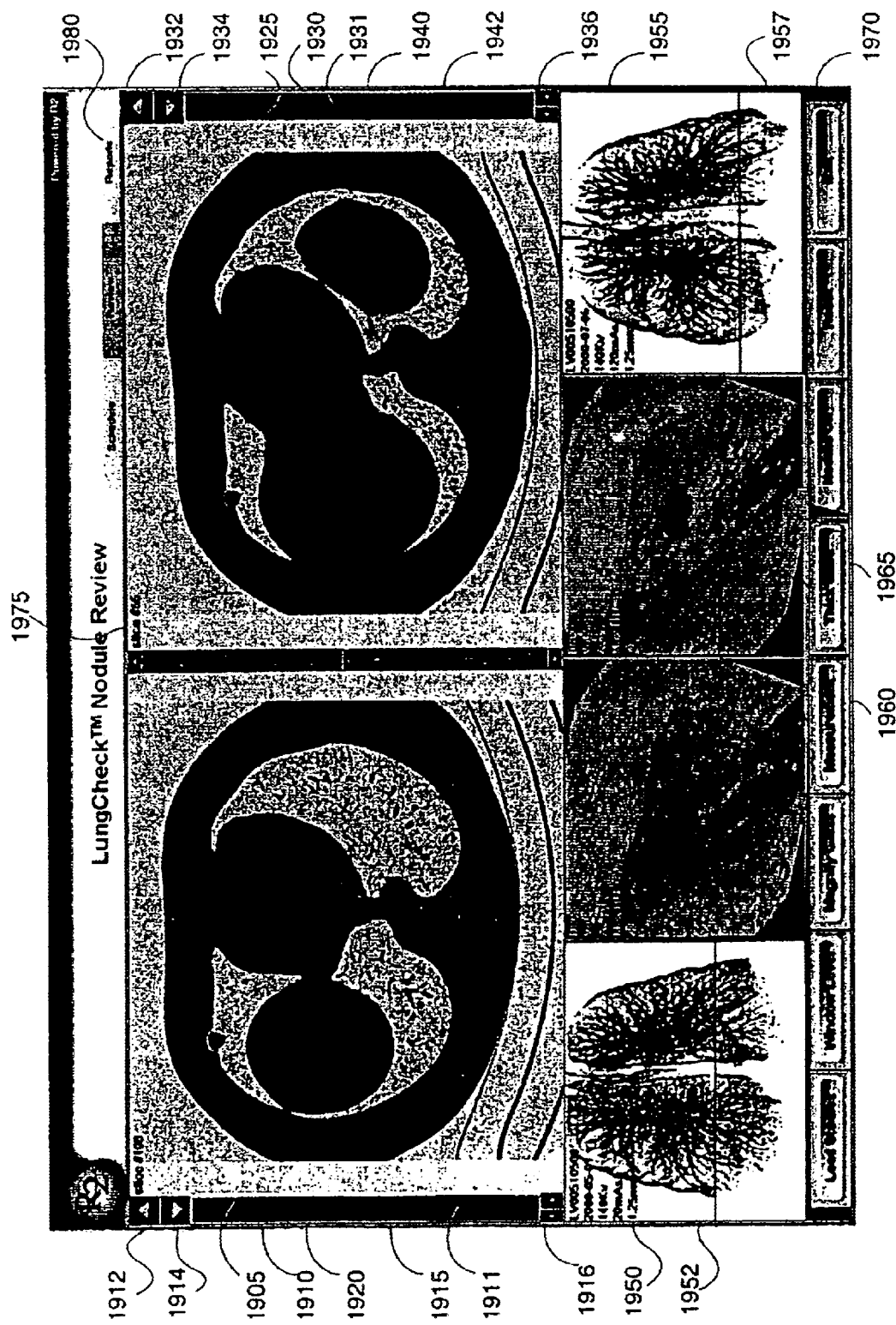
FIG. 19 is an illustration of a computer display of the present invention that provides for display of temporal data.

FIG. 19 is a view of an alternative preferred embodiment of a display that provides for the display of temporal information. By presenting views taken at different times, the physician is able to assess any changes that have taken place in a ROI. The display has portions associated with scanning information from a current scan and a second portion associated with scan results from a prior scan. For example, a first portion can include a first display 1905 of CT axial sections, a second display 1950 that is a volumetric view of the volume encompassed by the CT axial sections, a third display 1960 that is a magnified and rotatable portion of part of the volume rendered in the second display, and a navigator 1910 for moving between different axial sections, and automatically updating the volumetric sections for review as the axial sections are updated. The display in FIG. 19 also includes additional portions depicting temporal images relating to scanned images of the patient performed at a time different from that for the first portion: a first temporal display 1925 of CT axial sections, a second temporal display 1955 that is a volumetric view of the volume encompassed by the CT axial sections, a third temporal display 1965 that is a magnified and rotatable portion of part of the volume rendered in the second display and a navigator 1930 for moving between different axial sections, and automatically updating the volumetric sections for review as the axial sections are updated. The display in FIG. 19 also may preferably include a registered scroll bar 1975 that allows for concurrent movement and scrolling of the images in the displays 1905 and 1925. At the bottom of the display is a series of function buttons 1970 that operate similar to those of the display of FIG. 5.

Navigators 1910 and 1930 offer similar functionality to that of the other navigators described herein, for example, navigator 540. The first navigator preferably includes a first set of up and down scroll buttons 1912 and 1914, and a second set of left and right scroll buttons 1916. Display bar 1911 is a visual display of the vector of slice numbers that contain a ROI. Each slice number is represented in the display by a horizontal line such as horizontal line 1920. The axial section then being displayed in display 1905 is indicated by a white line 1915. The other horizontal lines are dark. The lines are spaced apart by an amount proportional to their distance from each other in the complete case of axial sections.

The second navigator preferably includes a first set of up and down scroll buttons 1932 and 1934, and a second set of left and right scroll buttons 1936. Display bar 1931 is a visual display of the vector of slice numbers that contain a ROI. Each slice number is represented in the display by a horizontal line such as horizontal line 1940. The axial section then being displayed in display 1905 is indicated by a white line 1942. The other horizontal lines are dark. The lines are spaced apart by an amount proportional to their distance from each other in the complete case of axial sections. Lines 1952 and 1957 correspond to relative volumetric locations in the images of second display 1950 and second temporal display 1955 of the axial sections as displayed in the first display 1905 and first temporal display 1930, respectively.

Each display window is independently controllable by navigator 1910 or 1930. Alternatively, the images can be scrolled simultaneously via navigation scroll bar 1975 which overrides the first and second set of scroll bars to update images in the display windows concurrently and allows users to compare images in corresponding windows concurrently.

As will be apparent to one skilled in the art, the temporal display images can be extended to include images taken at a third or fourth time, etc. so that qualified personnel would be able to track, monitor and/or diagnose a patient's progress over several different times. Corresponding scroll bars can be appropriately included.

While the temporal display images allow for a comparison of images taken of a patient at different times, in a further embodiment a cross-comparison display allows for the comparison of an image taken from a patient with an image of healthy tissue. In this way, the image taken of a patient can be easily compared against tissue representative of a healthy anatomy for assessing whether the patient's image is one of healthy or unhealthy tissue. The comparison can be simply visual or the comparison can be automated to determine whether the differences between the patient's image and the related cross-patient image indicative of healthy tissue exceeds acceptable thresholds. For example, a doctor can place one or more markers at a location on the patient image and place a corresponding marker at a location on the cross-comparison, or healthy tissue image. Differences in dimensions or intensity levels may be indicated in a margin or generated in a report (see FIG. 21).

Figure 20:
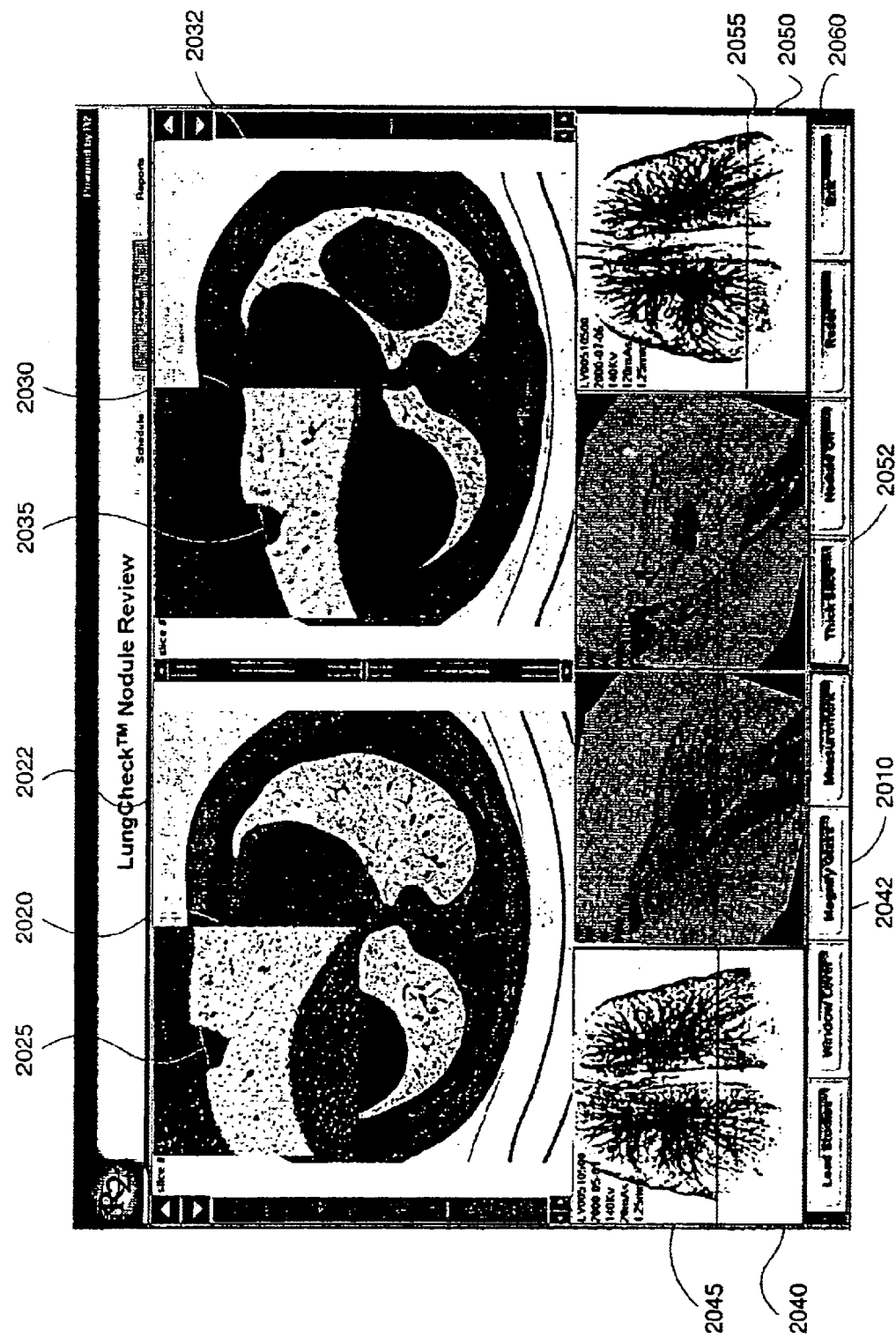
FIG. 20 is an illustration of a computer display of the present invention that provides for display of temporal data with the magnification feature activated.

FIG. 20 is a view of the embodiment of FIG. 19 with the magnification feature activated via button 2010. FIG. 20 includes a first set of images associated with a first scan of a body. The first set of images is depicted in displays 2022, 2040 and 2042. FIG. 20 also includes a second set of images associated with a second scan of a body taken at a different time (temporal images). The second set of images is depicted in displays 2032, 2050 and 2052. The display preferably include an array 2060 of feature buttons. Preferably, the magnification feature is activated at a location on an image in a display where the cursor is clicked. When clicked, a configurable magnification window is exposed at the location. As shown in FIG. 20, the cursor can be clicked in the first display window 2022 to expose a first magnification window 2020. In the first magnification window, nodule outline 2025 is shown, similar to outline 940 described above. The outline is preferably formed on the basis of differing contrast levels between the bright nodule and the dark background. If no nodule is in the magnification window, the outline 2025 will not automatically appear. At the same time the first magnification window 2020 appears, the display of FIG. 20 is preferably configured so that a second magnification window 2030 appears along with outline 2035, if appropriate. The display of the second magnification window 2030 about a nodule can be based on feature detection analysis of the nodule or other known features of the image in first magnification window 2020 for a corresponding nodule or feature in the first temporal window. As can be seen from a comparison of displays 2040 and 2050, a highlighted nodule may appear at different relative locations within the windows over time. Lines 2045 and 2055 in displays 2040 and 2050, corresponding to the volumetric location of the images in displays 2022 and 2032, respectively, are not necessarily at a same level within the display. The nodule outlines allow for detailed measurements of nodule size and for visual comparison of any changes of nodule shape or growth that may have taken place over time. Such visual comparisons facilitate diagnoses and/or the tracking of the effects of treatment.

Figure 21:
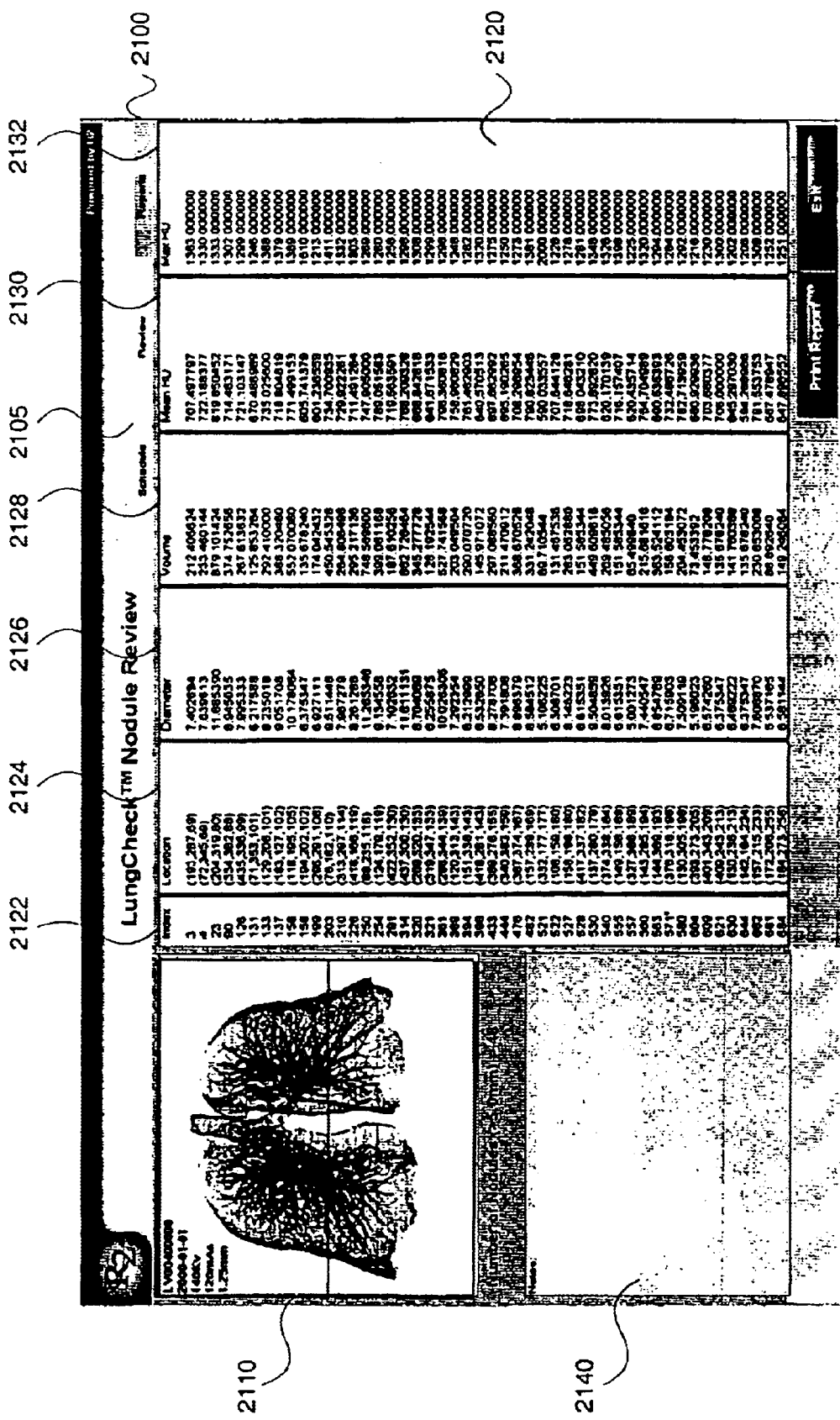
FIG. 21 is an illustration of the report feature that is activated upon clicking a seventh button on the display of FIG. 5.

FIG. 21 is a representation of a sample report that can be generated when the report button is activated, such as button 559 or 1980. The display preferably includes a first display window 2110 for depicting a volumetric representation of scanned images, a report window 2120 displaying selected information corresponding to various detected, selected or highlighted nodules and a notes window 2140 for inputting comments or notes related to the diagnosis. Report window 2120 preferably displays in index column 2122 a list of nodules indexed against the slice number containing the nodule. The window also preferably displays reference coordinates in location column 2124 for corresponding nodules in the index column, corresponding approximate nodule diameters in diameter column 2126, corresponding nodule volumes in volume column 2128, mean voxel intensity levels in column 2130 based on a standardized scale and maximum voxel intensity levels in column 2132 based on a standardized scale. Other columns can be added or removed. For example, in the case where temporal images (images taken of a body at different times) are being viewed, columns indicating nodule volume and diameter change or percentage change over time can be displayed. In this way, the growth or reduction of individual nodules can be tracked and monitored throughout treatment or diagnosis. Additionally, nodules can be selectively highlighted. For example, nodules above a preselected size can be highlighted. Moreover, the data in any column of a report is preferably sortable. The print report button 2150 allows for a print out of a nodule report. Additionally or alternatively, a save button can be implemented to allow for saving of the nodule information on disk or other recording media. Button 2100 allows the system to return to a prior display configuration.

Any of the display portions described herein can include numerical information within the display associated with any part of image then being rendered. For example, the diameter, volume, and intensity values can represented for a selected nodule highlighted by a marker. Additionally, probability values, in numerical form and/or analog form, may be provided and associated with the markers for detected or suspected abnormalities.

Preferably, the various interfaces are implemented based on touch-screen technology. Touch screens may be activated by touch and may or may not necessitate or include use of a mouse or other controller to navigate the interface. For example, a standard resistive display can be used where a controller and a specially-coated screen or glass overlay produce a touch connection. Such resistive displays allow for access via various input tools such as a finger, gloved finger, stylus and/or pen.

Preferably, a capacitive touch screen is used. Capacitive touch screens are generally all glass and more durable. For such screens a small current of electricity runs across the screen, and touching the screen interrupts the current and activates the screen. Such a screen is only activated by a human finger; a gloved finger, stylus or pen will not usually activate the screen.

Yet other types of touch screens can be based on surface-acoustic-wave (SAW) technology. Such SAW-based screens use mechanical waves on the surface of the glass to provide superior optical performance. When the screen is touched by a finger, gloved finger, pen and/or stylus, a mechanical wave is absorbed. Since a wave must be absorbed, SAW-based screens are resistant to false touch activations.

Medical applications also use infrared technology to implement high-end touch screens. Such screens rely on the interruption of an infrared light in the front of a display screen. Such screens can be sealed and activated by a finger, gloved finger, pen or stylus.

Because medical imaging equipment typically must interoperate with other medical devices, it is common for CT scanners and other medical imaging devices, displays and software to be interoperable and exchange data based on a common standard or protocol. For example, one such protocol is the DICOM standard, published by National Electrical Manufacturers Association, 1300 N. 17th Street, Rosslyn, Va. 22209 USA. A current final draft of this standard is publicly available at http://medical.nema.org/dicom/2000.html. The DICOM standard includes syntax and semantics of commands and associated information which can be exchanged by devices, particularly medical imaging equipment using the protocol. By using an interoperability standard, the exchange of digital information between medical imaging equipment can be facilitated. Preferably, the various interfaces described herein are based on a standard such as the DICOM standard. Implementation based on a standard supports the development of a conformance statement wherein a system is defined and where interoperability can be expected with another device claiming conformance to the standard. In this way, an interface can be configurable with various types and models of equipment conforming to the standard.

In another embodiment, hard copy or printed images are produced responsive to a command. Responsive to a command such as by touching a touch screen or by using another type of input device such as a keyboard or mouse, a high resolution image is printed using a printer. The printed image includes highlighting by applying a distinctive color such as white or red to the identified pixels. Moreover, in an embodiment, a close-up view is printed responsive to a command such that the printed radiographic image is shown at high resolution and the highlighting is also shown at high resolution. A radiologist can then use the printed radiographic image to supplement his evaluation of the digitized radiographic images as well as the actual radiographic films.

As will be apparent to those skilled in the art, numerous modifications may be made in the display of the present invention that are within the scope and spirit of the invention. While the invention has been described in a particular context of CT scanning of the lungs to detect potentially cancerous regions, the invention may also be used to display the results of CT scanning of other regions of the body and for other applications as well as to display the results of other scanning technologies such as ultrasound imaging and magnetic resonance imaging. For example, the invention described herein could apply other organs and anatomical parts including, without limitation, the heart, brain, spine, colon, kidney and liver.

What is claimed:

1. A method for rendering anatomical information of a body from tomographic data comprising the steps of:

receiving said tomographic data obtained from a digital imaging apparatus wherein said tomographic data is displayable in a first portion of a display as one or more two-dimensional tomographic sections of a sequence of two-dimensional tomographic sections;

determining a third dimension from the sequence of two-dimensional tomographic sections to create a first volumetric view wherein said first volumetric view is displayable in a second portion of the display;

determining a second volumetric view of a selected feature shown in the first or second portion wherein said second volumetric view is displayable in a third portion of the display; and rendering one or more of said first, second or third portions of the display.

2. The method of claim 1 further including the step of providing on-off toggle whereby any of the display portions can be toggled on to display anatomical information or toggled off to remove from display the corresponding display portion.

3. The method of claim 2 further including the step of providing a scroll bar whenever the first display is toggled on, for selecting the particular two-dimensional tomographic section to be displayed in the first display portion.

4. The method of claim 1 wherein the step of rendering further includes providing display markers indicative of a region of interest in the body.

5. The method of claim 1 wherein the step of rendering further includes providing display markers indicative of a potentially cancerous nodule in the body.

6. The method of claim 1 wherein anatomical information is rendered in the first and second portion of the display.

7. The method of claim 6 further comprising the step of updating the anatomical information in the second display portion in response to a region of interest or an image rendered in the first portion of the display.

8. The method of claim 6 further comprising the step of updating the anatomical information in the first display portion in response to an image rendered in the second portion of the display.

9. The method of claim 1 wherein anatomical information occurs in the first and third portions of the display.

10. The method of claim 9 further comprising the step of updating the anatomical information in the first display portion in response to a region of interest or an image rendered in the third portion of the display.

11. The method of claim 9 further comprising the step of updating the anatomical information in the third display portion in response to an image rendered in the first portion of the display.

12. The method of claim 1 wherein anatomical information occurs in the second and third portions of the display.

13. The method of claim 12 further comprising the step of updating the anatomical information in the second display portion in response to a region of interest or an image rendered in the third portion of the display.

14. The method of claim 12 further comprising the step of updating the anatomical information in the third display portion in response to a region of interest or an image rendered in the second portion of the display.

15. The method of claim 1 wherein anatomical information occurs in the first, second and third portions of the display.

16. The method of claim 15 further comprising the step of updating the anatomical information in a display portion in response to the region of interest or the image rendered in a different portion of the display.

17. The method of claim 15 further including the step of providing a scroll bar for selecting the particular two-dimensional tomographic section to be displayed in the first display portion.

18. A system for rendering anatomical information of a body from tomographic data obtained from a digital imaging apparatus comprising:

a first portion of a display for rendering a sequence of two-dimensional tomographic sections obtained from said tomographic data;

a second portion of the display for rendering a first volumetric view of the body wherein said first volumetric view is includes a third dimension acquired from the sequence of two-dimensional tomographic sections; and a third portion of the display for rendering a second volumetric view of a selected feature shown in the section then being rendered on the first portion or second portion of the display.

19. The graphical user interface of claim 18 further comprising a fourth portion of the display for indicating the relative position of axial sections containing features of interest, said scroll buttons enabling a user to increment all displays (axial and volumetric) from one section to another.

20. The system of claim 18 wherein the view of the third portion is rotatable by input from a trackball or cursor.

21. The system of claim 18 wherein the particular section being rendered at any time in the first portion is selectable by means of a scroll bar or scroll buttons.

22. The system of claim 18 wherein the first portion of the display includes at least one first display marker indicative of a region of interest in the body.

23. The system of claim 22 wherein at least one second display marker is displayed in the second portion of the display at a location in the second portion of the display corresponding to the same location in the body as at least one first display marker.

24. The system of claim 22 wherein the region of interest includes a potentially cancerous nodule.

25. The system of claim 18 wherein said second portion includes an indication on said volumetric view of the position of the section then being rendered on the first portion of the display.

26. The system of claim 18 wherein said volumetric view of the third portion of the display is selectively rotatable so as to render information in the least one tomographic section adjacent to the section then being rendered on the first portion of the display.

27. The system of claim 18 wherein the first portion of the display includes at least one first display marker and wherein the second portion of the display includes at least one second display marker, said first display marker and said second display marker corresponding to the same location in the body.

28. The system of claim 27 wherein a first display marker is highlighted.

29. The system of claim 28 wherein a second display marker is highlighted corresponding to the same location in the body as identified by the highlighted first display marker.

30. The system of claim 27 wherein the first display marker is responsive to the second display marker.

31. The system of claim 27 wherein the second display marker is responsive to the first display marker.

32. The system of claim 27 wherein the third portion of the display includes a third display marker corresponding to the same location in the body as highlighted by the first display marker or the second display marker.

33. The system of claim 32 wherein the third display marker is responsive to the first display marker or second display marker.

34. The system of claim 18 wherein the first portion of the display includes at least one first display marker and wherein the second portion of the display includes one second display marker and wherein the third portion of the display includes one third display marker, said at least one first display marker defining a first region of interest, said at least second display marker defining a second region of interest and said at least third display marker defining a third region of interest wherein said first region of interest, said second region of interest and said third region of interest correspond to the same location of the body.

35. The system of claim 34 wherein said first region of interest, said second region of interest and said third region of interest include a first nodule, second nodule and third nodule, respectively.

36. The system of claim 35 wherein the first nodule, second nodule and third nodule correspond to a nodule in the body.

37. The system of claim 36 wherein the nodule is potentially cancerous.

38. The system of claim 18 wherein the interface displays a slice number identifying a CT axial scan.

39. The system of claim 18 further including a fourth portion of the display, said fourth portion displaying patient information.

40. The system of claim 18 further including a fourth portion of the display, said fourth portion when activated displaying a magnification box for displaying an enlarged view of a selected region.

41. The system of claim 40 wherein the magnification box is configurable.

42. The system of claim 40 wherein the magnification box has a center corresponding to a location defined by a marker.

43. The system of claim 40 wherein the magnification box is displayed within the first portion of the display.

44. The system of claim 40 wherein the enlarged view includes a nodule in the tomographic axial section highlighted by an outline defining the shape of the nodule.

45. The system of claim 40 wherein a cursor may be positioned at a first location within the enlarged view and dragged to a second location, the distance between the first location and second location being displayed on the interface.

46. The system of claim 18 wherein the first portion of a display renders an image formed from a composite of more than one tomographic axial section.

47. The system of claim 18 further including a fourth portion of the display, said fourth portion when activated displaying thick slices.

48. The system of claim 18 further including a fourth portion of the display, said fourth portion when activated displaying markers in said first portion, said second portion and said third portion of the display.

49. The system of claim 18 further including a fourth portion of the display, said fourth portion when activated removing from display any markers in said first portion, said second portion and said third portion of the display.

50. The system of claim 18 further including a navigation tool.

51. The system of claim 50 wherein the navigation tool includes identifiers graphically corresponding to at least one tomographic axial section displaying a nodule when said tomographic axial section is rendered in the first portion.

52. The system of claim 51 wherein the navigation tool includes means for rendering the tomographic axial section adjacent to the section then being rendered in the first portion of the display.

53. The system of claim 50 wherein the navigation tool includes an identifier graphically corresponding the relative location of the tomographic axial section then being rendered in the first display within the sequence of tomographic axial section.

54. The system of claim 50 wherein the navigation tool includes means for rendering a sequence of tomographic axial sections.

55. The system of claim 51 wherein the views rendered in the second portion of the display are responsive to the particular tomographic axial section then rendered in the first portion.

56. The system of claim 50 wherein an identifier on the navigator tool when selected displays the tomographic axial section in the first display corresponding to said identifier.

57. The system of claim 18 further including a fourth portion of the display, said fourth portion when activated allowing a cursor to be positioned at a first location in the first display and dragged to a second location, the distance between the first location and second location being displayed on the interface.

58. The system of claim 18 further including a fourth portion of the display, said fourth portion when activated displaying a report relating to images displayed in the interface.

59. The system of claim 58 wherein the report includes reference coordinates corresponding to the relative location of the one or more nodules.

60. The system of claim 58 wherein the report includes the radius of at least one nodule.

61. The system of claim 58 wherein the report includes the calculated volume of at least one nodule.

62. The system of claim 58 wherein the report includes the relative intensity of at least one nodule.

63. The system of claim 58 wherein the report includes the percentage change in volume of the size of at least one nodule over a period of time.

64. The system of claim 58 wherein the report includes the percentage change in radius of at least one nodule over a period of time.

65. The system of claim 18 further including a fourth portion of the display, said fourth portion when activated displaying a histogram of intensity levels within a selected region.

66. The system of claim 18 further including a fourth portion of a display for rendering a sequence of tomographic axial sections taken of the body, a fifth portion of the display for rendering a volumetric view of the body and corresponding to the images displayed in the fourth portion and a sixth portion of the display for rendering a volumetric view of a selected feature shown in the section then being rendered on the fourth portion of the display.

67. The system of claim 66 further including a first navigation tool associable with the first portion, second portion and third portion and a second navigation tool associable with the fourth portion, fifth portion and sixth portion.

68. The system of claim 67 wherein the first navigation tool includes means for rendering a sequence of tomographic axial sections renderable in the first display.

69. The system of claim 68 wherein the second navigation tool includes means for rendering a sequence of tomographic axial sections renderable in the fourth display.

70. The system of claim 67 further including a third navigation tool wherein said third navigation tool includes means for rendering a sequence of tomographic axial sections renderable in the first display simultaneously with the rendering of a sequence of tomographic axial sections renderable in the fourth display.

71. The system of claim 18 further including a fourth portion of the display, said fourth portion when activated displaying a schedule box for scheduling processing of image data.

72. The system of claim 66 further including a navigation tool wherein said navigation tool includes means for rendering a sequence of tomographic axial sections renderable in the first display simultaneously with rendering of a sequence of tomographic axial sections renderable in the fourth display.

73. A method for rendering anatomical information obtained by tomographic scanning of a body comprising:

rendering on a first portion of display a sequence of axial sections, the particular section being rendered at any time being selectable by means of a scroll bar or scroll buttons;

rendering on a second portion of the display a volumetric view of the body, said view including an indication of the position on the body of the section then being rendered on the first portion of the display; and rendering on a third portion of the display a view of a selected feature shown in the section then being rendered on the first portion, said view being selectively rotatable about multiple axes.

* * * * *